(12) United States Patent
Kornbluh et al.

(10) Patent No.: US 10,073,441 B1
(45) Date of Patent: *Sep. 11, 2018

(54) METHOD AND APPARATUS FOR MANAGING OXYGEN GENERATING SYSTEM

(71) Applicant: HVLPO2, LLC, Lincoln, NE (US)

(72) Inventors: Marc Kornbluh, Lincoln, NE (US); Thomas D. Friedman, Omaha, NE (US); Eric Ellenwood, Lincoln, NE (US)

(73) Assignee: HVLPO2, LLC, Lincoln, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/156,798

(22) Filed: May 17, 2016

Related U.S. Application Data

(60) Continuation of application No. 14/502,279, filed on Sep. 30, 2014, now Pat. No. 9,372,488, which is a continuation of application No. 14/248,824, filed on Apr. 9, 2014, now Pat. No. 8,876,941, which is a continuation of application No. 14/179,105, filed on
(Continued)

(51) Int. Cl.
  *B01D 53/04* (2006.01)
  *G05B 19/4155* (2006.01)
  *C01B 13/02* (2006.01)

(52) U.S. Cl.
  CPC ...... *G05B 19/4155* (2013.01); *C01B 13/0248* (2013.01); *B01D 2256/12* (2013.01); *G05B 2219/37371* (2013.01)

(58) Field of Classification Search
  CPC ............... B01D 53/02; B01D 2256/12; G05D 19/4155; G05D 2219/37371; C01B 13/02; C01B 13/0248

USPC .......... 95/1, 19, 22, 54, 130; 96/4–14, 109, 96/113, 121; 128/204.18, 205.12, 205.27
See application file for complete search history.

(56) References Cited

U.S. PATENT DOCUMENTS 2,944,627 A 7/1960 Skarstom
3,860,396 A 1/1975 Finley
(Continued)

FOREIGN PATENT DOCUMENTS

EP 1245267 A1 10/2002
GB 2397374 7/2004

OTHER PUBLICATIONS

Machine-generated English translation of EP 1245267 A1, published Oct. 2002.
(Continued)

*Primary Examiner* — Frank Lawrence
(74) *Attorney, Agent, or Firm* — Suiter Swantz pc llo

(57) ABSTRACT

A system for managing an oxygen generating system including an oxygen storage tank, a compressor, and groups of at least one oxygen generator, wherein the oxygen generating system is configured for supplying a sustained flow of a gaseous mixture comprising mostly oxygen. The system includes at least one controller device. The at least one controller device is configured to control group circuits based at least upon a pressure. Each of the group circuits are for providing power to a particular group of the groups of at least one oxygen generator. The at least one controller device is also configured to control a circuit for providing power to the compressor.

23 Claims, 13 Drawing Sheets

Related U.S. Application Data

Feb. 12, 2014, now Pat. No. 9,139,434, which is a division of application No. 13/592,875, filed on Aug. 23, 2012, now Pat. No. 8,702,840.

(60) Provisional application No. 61/583,051, filed on Jan. 4, 2012.

(56) References Cited

U.S. PATENT DOCUMENTS

| | | | |
|---|---|---|---|
| 4,509,959 A | 4/1985 | McCombs | |
| 4,584,001 A | 4/1986 | Dechene | |
| 5,154,737 A | 10/1992 | Jenkins et al. | |
| 6,368,491 B1 | 4/2002 | Cao et al. | |
| 6,394,089 B1 | 5/2002 | Cantrill et al. | |
| 7,922,789 B1 | 4/2011 | Deane et al. | |
| 8,424,525 B2 | 4/2013 | Peacey et al. | |
| 8,603,228 B2 | 12/2013 | Wilkinson et al. | |
| 8,702,840 B1 | 4/2014 | Friedman et al. | |
| 9,139,434 B1 * | 9/2015 | Friedman | B01D 53/053 |
| 9,372,488 B1 * | 6/2016 | Kornbluh | B01D 53/053 |
| 2003/0167924 A1 | 9/2003 | McCombs | |
| 2004/0211414 A1 | 10/2004 | Cantrill et al. | |
| 2008/0170953 A1 | 7/2008 | Lund | |

OTHER PUBLICATIONS

"Mid-Size Oxygen Generator Model OG-25"; Oxygen Generating Systems Intl., printed from website http://www.ogsi.com/mid_size.php, Dec. 6, 2011, 2 pages.
"OGSI Introduces the OG-20 Oxygen Generating System"; Oxygen Generating Systems Int., printed from website http://www.ogsi.com/og_20.php, Dec. 7, 2011, 1 page.
"Eliminate the Costs of Transportation, Storage and Cylinder Rental"; Oxygen Generating Systems Intl., printed from website http://www.ogsi.com/ogs_20.php, Dec. 7, 2011, 1 page.
"Lower Your Facility's Operating Costs . . . Take Oxygen Directly from the Air!"; Oxygen Generating Systems Intl., printed from website http://www.ogsi.com/hospital_systems.php, Dec. 6, 2011, 2 pages.
"Convenient Onsite Oxygen Generation and Cylinder Filling"; Oxygen Generating Systems, Intl., printed from website http://www.ogsi.com/mogs_50_100.php, Dec. 6, 2011, 1 page.
OGSI Oxygen Generators Product Data Sheet, *Oxygen Generating Systems Intl., HVLPO2, LLC v Oxygen Frog, LLC et al.* United States District Court for the District of Nebraska, Defendant's Motion for Transfer of Venue, Case No. 8:15-cv-00176-JMG-CRZ, Doc # 10, pp. 5-6, Publication date unknown, Filed Jun. 4, 2015 Printed Mar. 30, 2016.
AirSep, A Chart Industries Company, PSA Oxygen Generator AS-A, *HVLPO2, LLC v Oxygen Frog, LLC et al.* United States District Court for the District of Nebraska, Defendant's Motion for Transfer of Venue, Case No. 8:15-cv-00176-JMG-CRZ, Doc # 10, pp. 7-8, Publication date unknown, Filed Jun. 4, 2015, Printed Mar. 30, 2016.
Photograph, *HVLPO2, LLC v Oxygen Frog, LLC et al.* United States District Court for the District of Nebraska, Defendant's Motion for Transfer of Venue, Case No. 8:15-cv-00176-JMG-CRZ, Doc # 10, p. 9, Publication date unknown, Filed Jun. 4, 2015, Printed Mar. 30, 2016.
Low Tide Glass, Oxygen Concentrator System, YouTube.com, https://www.youtube.com/watch?v=JSJF9Jhf79Y, Publication date unknown, Uploaded to YouTube Sep. 1, 2010, Printed online Mar. 20, 2016, 3 pages.
Jelsoft Enterprises Ltd., The Melting Pot, The Melting Pot Discussion Forums, Glass Discussion, Thread: Another oxy gen????, Publication Date Unknown, Posted online Jan. 8, 2010, Downloaded Aug. 25, 2016, 9 pages.
TE Connectivity, Contractor Outline 3P 60 FLA with 24 Vac Coil, TE Part No. 4-1611022-8, Drawing No. C-3100-30I17999CJ, Dated Jun. 22, 2011, Downloaded Aug. 25, 2016, 1 page.
Trey Cornette, Declaration of Trey Cornette, United States District Court for the Northern District of Florida Tallahassee Division, Case No. 4:16-cv-00336-MW-CAS, *HVLPO2, LLC v. Oxygen Frog, LLC and Scott D. Fleischman*, Dated Feb. 15, 2018, 4 pages.
Crydom Inc., Data Sheets, DRA4D and DP Series, Publication Date Unknown, Downloaded Aug. 25, 2016, 13 pages.
Dwyer, MDPC Series Pressure Controller Instruction Sheet, Publication Date Unknown, Downloaded Aug. 25, 2016, 6 pages.
Jelsoft Enterprises Ltd., The Melting Pot, The Melting Pot Discussion Forums, Glass Discussion, Thread: EX2000 oxygen filler, Publication Date Unknown, Posted online Feb. 19, 2010, Downloaded Sep. 13, 2016, 13 pages.
Siew Wah Chai, Experimental Simulation of Rapid Pressure Swing Adsorption for Medical Oxygen Concentrator and Numerical Simulation of the Critical Desorption-by-Purge Step, Submitted Sep. 2011, Lehigh University, Lehigh Preserve, Theses and Dissertations, 410 pages.
Jelsoft Enterprises Ltd., Lampwork Etc., Library, Tips, Techniques, and Questions, Torch Questions Thread: Problem with EXO2 filling station, Publication Date Unknown, Posted online Jul. 12, 2009, Downloaded Aug. 25, 2016, 12 pages.
Oxygen Generating Systems Intl. (OGSI), Divisional of Audubon Machinery Corporation, OGS-20 Oxygen Generator, Installation, Operation and Maintenance Manual, Publication Date Unknown, Downloaded Aug. 25, 2016, 41 pages.
Automationdirect.com, ProSense Digital Pressure Switch/Transmitter Instructions for Models: QPSL-AP-42, OPSL-AN-42, QPSH-AP-42, and QPSH-AN-42, Publication Date Unknown, Downloaded Aug. 25, 2016, pp. 1-4.
Tyco Electronics, Model 93-3100 Series, Catalog 1308242, Definite Purpose Contactor, 4-pole, 25-40 FLA, AC Coil, Publication Date Unknown, Downloaded Aug. 25, 2016, 2 pages.
Low Tide Glass, Oxygen Concentrator System, Stills and Transcript of YouTube.com video, https://www.youtube.com/watch?v=JSJF9Jhf79Y, Publication Date Unknown, Uploaded to YouTube Sep. 1, 2010, Printed Online Mar. 20, 2016.

* cited by examiner

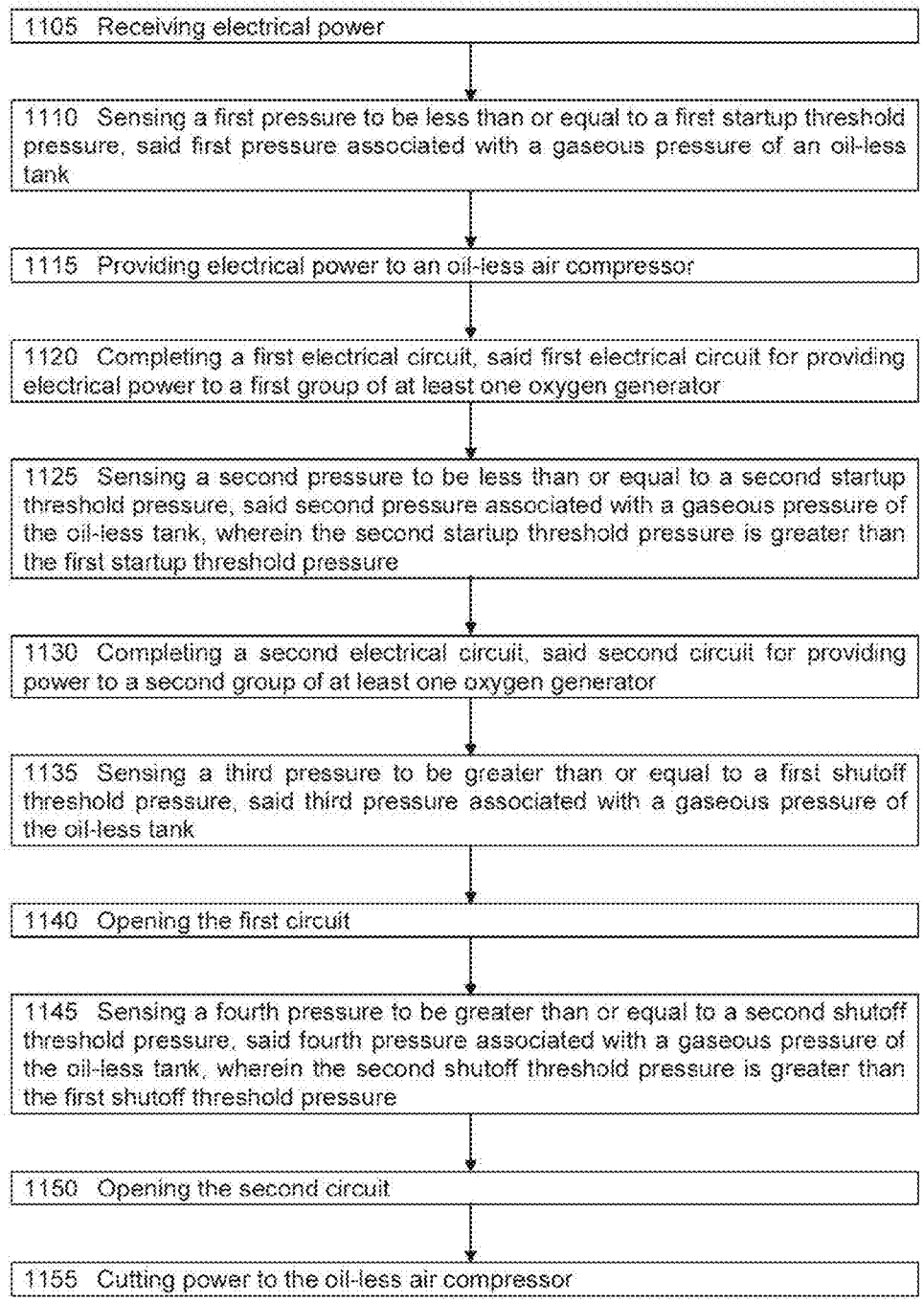

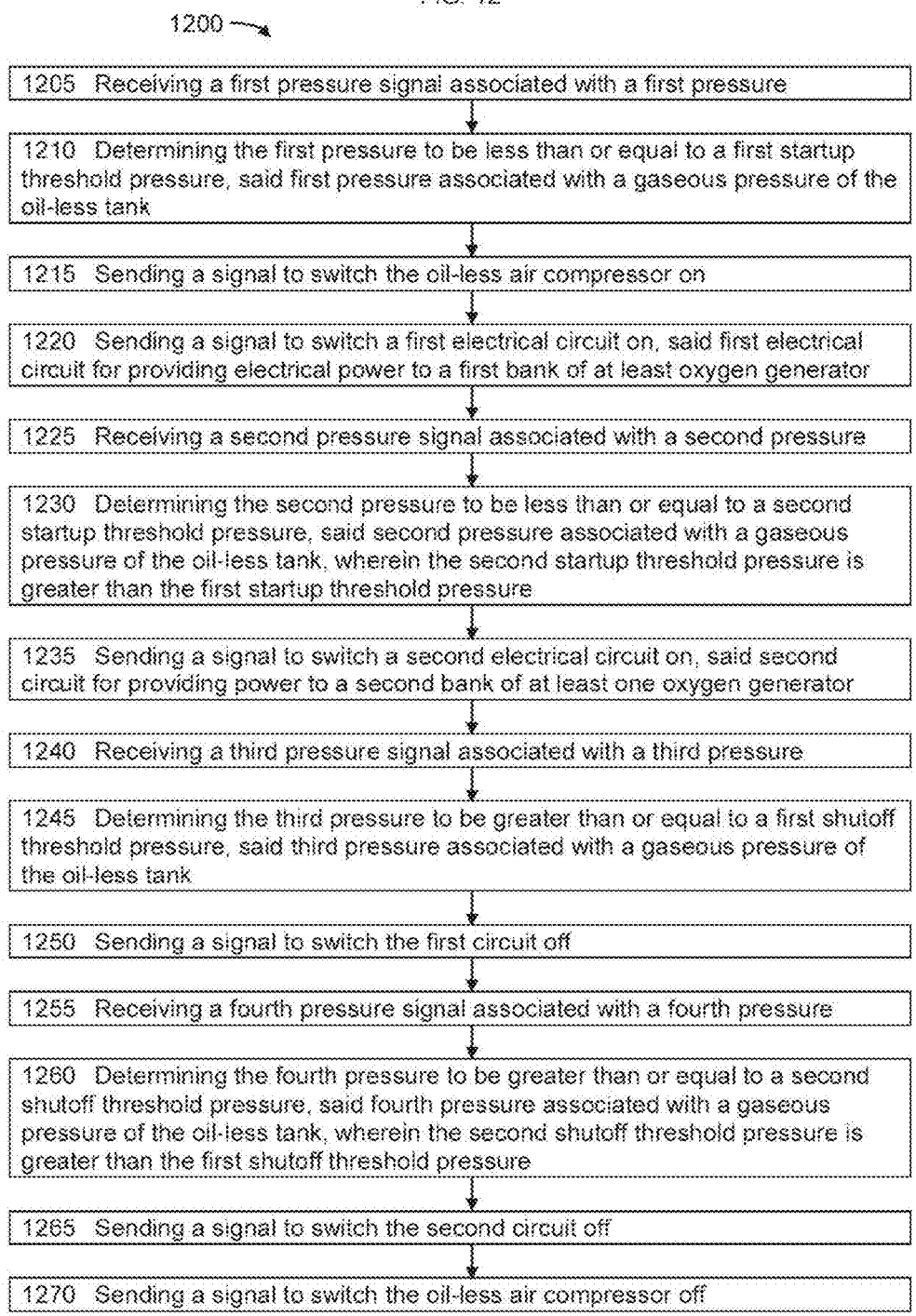

METHOD AND APPARATUS FOR MANAGING OXYGEN GENERATING SYSTEM

CROSS-REFERENCE TO RELATED APPLICATIONS

The present application claims priority under 35 U.S.C. § 120 as a continuation application of U.S. patent application Ser. No. 14/502,279, filed Sep. 30, 2014 and issued as U.S. Pat. No. 9,372,488 on Jun. 21, 2016, which claims priority under 35 U.S.C. § 120 to U.S. patent application Ser. No. 14/248,824, filed on Apr. 9, 2014 and issued as U.S. Pat. No. 8,876,941 on Nov. 4, 2014, which claims priority under 35 U.S.C. § 120 to U.S. patent application Ser. No. 14/179,105, filed on Feb. 12, 2014 and issued as U.S. Pat. No. 9,139,434 on Sep. 22, 2015, which claims priority under 35 U.S.C. § 120 to U.S. patent application Ser. No. 13/592,875, filed on Aug. 23, 2012 and issued as U.S. Pat. No. 8,702,840 on Apr. 22, 2014, which claims the benefit under 35 U.S.C. § 119(e) of U.S. Provisional Application Ser. No. 61/583,051, filed Jan. 4, 2012; U.S. patent application Ser. Nos. 13/592,875, 14/179,105, 14/248,824, and 14/502,279 and U.S. Provisional Application Ser. No. 61/583,051 are herein incorporated by reference in their entirety.

FIELD OF THE INVENTION

The present invention is directed generally toward systems, devices, controls, or methods for oxygen generation, oxygen storage, and/or oxygen supply configured to supply sustained high oxygen flow output or high oxygen output volumes.

BACKGROUND OF THE INVENTION

A continuous high-flow oxygen supply is critical for torch glass artists who use surface mix glass torches. Surface mix glass torches mix propane and oxygen creating a controlled flame in the temperature range of approximately 2,500 and 3,000 Fahrenheit. Glass torches typically need a constant supply of fairly pure oxygen (90-95% pure) at 20 to 30 pounds per square inch (psi) depending upon the model of the glass torch. Larger torches may consume 15 to 25 liters per minute (lpm) of oxygen at that pressure. Oxygen generators (also known as oxygen concentrators) on the market fail to provide the necessary pressure and/or volume required by larger glass torches used for working with large borosilicate glass ("boro") pieces. Only very expensive larger systems (such as systems for hospitals and universities) provide the necessary pressure and/or volume of oxygen for working with large borosilicate glass pieces with larger glass torches.

Torch glass artists rely upon gas distributors who rent "K-tanks" of oxygen. These K-tanks can be returned for refills when needed. A full K-tank contains oxygen pressurized to 2,200 psi and needs a regulator to reduce the pressure to a desired pressure (e.g., 30 psi). A glass torch artist may utilize an entire K-tank of oxygen within a day or even a few hours depending on a particular project which the artist is working on. Relying on K-tanks is expensive. Other problems associated with bottled gas include transport and storage hazards, availability, waiting for tank delivery, running out of oxygen mid-project, or dangers associated with changing oxygen tanks mid-project.

Currently there is no cost efficient oxygen generator system capable of producing a constant source of oxygen for use at sufficient oxygen flow and pressure; additionally, there are no oxygen generating systems which can be used with nominal 110 volt outlets without overloading a residential circuit breaker. Therefore, it may be desirable to provide a method, apparatus, and system which address the above-referenced problems.

SUMMARY OF THE INVENTION

Accordingly, an embodiment includes a system for managing an oxygen generating system. The oxygen generating system includes an oxygen storage tank, a compressor, and groups of at least one oxygen generator. The oxygen generating system is configured for supplying a sustained flow of a gaseous mixture comprising mostly oxygen. The system includes at least one controller device. The at least one controller device is configured to control group circuits based at least upon a pressure. Each of the group circuits are for providing power to a particular group of the groups of at least one oxygen generator. The at least one controller device is also configured to control a circuit for providing power to the compressor.

Accordingly, an embodiment includes a system for managing a modularly expandable oxygen generating system, wherein the modularly expandable oxygen generating system includes a main oxygen generating system an expansion oxygen generating system. The system includes at least one controller device. The at least one controller device is configured to manage the main oxygen generating system, wherein the main oxygen generating system includes a main system oxygen storage tank, a main system compressor, and main system groups of at least one oxygen generator. The main oxygen generating system is configured to supply a sustained flow of a gaseous mixture comprising mostly oxygen. The at least one controller device being configured to manage the main oxygen generating system includes the at least one controller device being configured to: control main system circuits, each for providing power to a particular group of the main system groups of at least one oxygen generator; and control an additional main system circuit for providing power to the main system compressor. The at least one controller device is further configured to manage the expansion oxygen generating system, wherein the expansion oxygen generating system includes an expansion system oxygen storage tank, an expansion system compressor, and at least one expansion system oxygen generator. The at least one controller device being configured to manage the expansion oxygen generating system includes the at least one controller device being configured to: control at least one expansion system circuit for providing power to the at least one expansion system oxygen generator; and control an additional expansion system circuit for providing power to the expansion system compressor.

Accordingly, an embodiment includes a system for managing an oxygen generating system. The oxygen generating system includes an oxygen storage tank, a compressor, and groups of at least one oxygen generator. The oxygen generating system is configured for supplying a sustained flow of a gaseous mixture comprising mostly oxygen. The system includes means for controlling group circuits based at least upon a pressure. Each of the group circuits are for providing power to a particular group of the groups of at least one oxygen generator. The system also includes means for controlling a circuit for providing power to the compressor.

It is to be understood that both the foregoing general description and the following detailed description are exemplary and explanatory only and are not restrictive of the invention claimed. The accompanying drawings, which are incorporated in and constitute a part of the specification, illustrate embodiments of the invention and together with the general description, serve to explain the principles.

BRIEF DESCRIPTION OF THE DRAWINGS

The numerous objects and advantages of the present invention may be better understood by those skilled in the art by reference to the accompanying figures in which:

FIG. 11 depicts a method for managing pressure of an oil-less tank of oxygen; and FIG. 12 depicts a method for managing pressure of an oil-less tank of oxygen.

DETAILED DESCRIPTION OF THE INVENTION

Figure 1A:
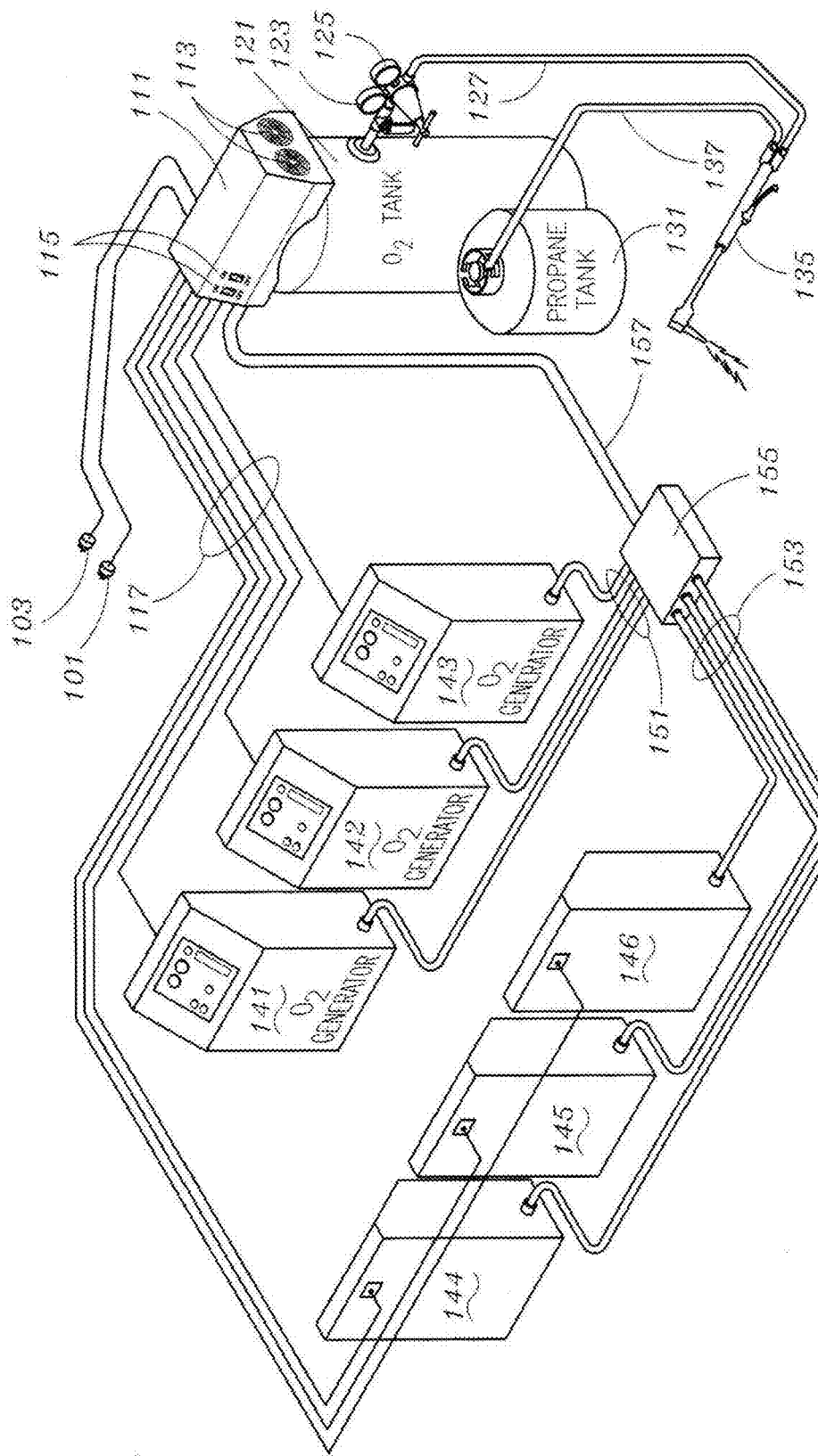
FIG. 1A shows a depiction of an embodiment of an oxygen generating system.

Reference will now be made in detail to the subject matter disclosed, which is illustrated in the accompanying drawings. The scope of the invention is limited only by the claims; numerous alternatives, modifications, and equivalents are encompassed. For the purpose of clarity, technical material that is known in the technical fields related to the embodiments has not been described in detail to avoid unnecessarily obscuring the description.

Embodiments of the invention may include an oxygen generating system, one or more components of the oxygen generating system, and methods of managing or controlling the oxygen generating system. The oxygen generating system may include a plurality of oxygen generators, a control box, an oxygen storage tank, and a vacuum pump compressor. Embodiments of the invention may further include the demodulation of a modular oxygen generating system into a plurality of independent oxygen generating systems; similarly, embodiments of the invention may include the demodulation of a modular oxygen generating system into a smaller modular oxygen generating system and one or more independent oxygen generating systems.

The vacuum pump compressor may be configured to draw oxygen from multiple oxygen generators (which produce oxygen at low pressures, such as between 5 and 15 psi), to compress the generated oxygen to a higher pressure (such as 80 to 100 psi), and then to pump the oxygen to an oxygen storage tank. Embodiments of the invention may include the modular expandability of a plurality of independent oxygen generating systems into a modular oxygen generating system, wherein the modular oxygen generating system includes a main control box and one or more drone control boxes.

Embodiments of the invention may include one or more control boxes. The control box may include one or more controller devices (such as a digital controller, analog controller, pressure switch, or pneumatic controller); a pump or compressor; one or more relays; one or more power cords configured to provide power; one or more power outlets (or banks or groups of outlets) configured to provide power to one or more oxygen generators; one or more oxygen inlet ports configured to receive oxygen from one or more oxygen generators; one or more oxygen outlet ports configured to supply oxygen from the pump or compressor to an oxygen storage tank; one or more pressure sensors or transducers; one or more valves (such as one or more of the following: safety release valves, shut-off valves, balancing valves, control valves, solenoid valves, pressure regulating valves, check valves, or solenoid safety valves).

In some implementations, the one or more control boxes may include one or more communication ports or jacks configured to send or receive communications or signals via one or more wires or cables (such as USB cables, Thunderbolt cables, FireWire, Ethernet cables, coaxial cables, optical fiber cables, or other wires or cables) to one or more of the following: to one or more other control boxes; to one or more remote relay and outlet boxes; to one or more other relays; to one or more control valves or solenoid valves; to one or more wired or wireless networks (such as a local area network (LAN) or a wireless area network (WAN)); to one or more storage devices; to one or more computing devices; or to one or more computer systems. In further implementations, the one or more control boxes may include one or more receivers and/or antennas configured to send and/or receive wireless communications or signals (including communications or signals sent or received via electromagnetic waves, such as via radio-frequency signals) to one or more of the following: to one or more other control boxes; to one or more remote relay and outlet boxes; to one or more other relays; to one or more control valves or solenoid valves; to one or more wired or wireless networks (such as a local area network (LAN) or a wireless area network (WAN)); to one or more storage devices; to one or more computing devices; or to one or more computer systems.

The control box may include an exterior case. The exterior case may include one or more openings, apertures, open surfaces, perforated surfaces, or grates. The exterior of the control box may further include one or more on/off buttons (such as on/off toggle switches). For example, the exterior of the control box may include a master on/off button, one or more on/off buttons configured to correspond to each power cord, one more on/off buttons configured to correspond to each group of power outlets configured to power one or more oxygen generators, and/or an on/off button configured to correspond to the pump or compressor. The exterior of the control box may also include controls for controlling or adjusting the oxygen generating system. The exterior of the control box may include a display (such as an LCD display). In some implementations, the display may be a touch-screen display and may include a user interface for displaying, controlling, or adjusting characteristics of components of the oxygen generating system. The display may be communicatively coupled with the digital controller and/or other computing devices, a computer system, or the like.

In some implementations, the one or more power cords may be removable or disconnectable from the control box such that one or more unused power cords can be disconnected. By way of example, the one or more power cords may include two removable or disconnectable 110 volt (nominal) power cords and one removable or disconnectable 220 volt (nominal) power cord. That is, for example, if the control box is receiving power via a 220 volt (nominal) power circuit, two or more 110 volt (nominal) power cords may be disconnected; on the other hand, if the control box is receiving power via two or more 110 volt (nominal) power circuits, the one or more 220 volt (nominal) power cord may be disconnected.

When one or more power cords are connected to the control box and plugged in to a power source, the power cords are configured to supply power from the power source to one or more components of the control box or oxygen generating system. For example, the one or more power cords may supply power to one or more controller device (such as a digital controller), a pump or compressor, one or more power outlets configured to provide power to oxygen generators, to one or more pressure sensors, to one or more receivers or antennas, or one or more other electrically powered components of the control box, or one or more electrically powered components receiving power from the control box.

In some implementations, the one or more power cords may be associated with a particular circuit or circuits. For example, a first power cord, which receives power from a first power source (e.g., a first nominal 110 volt power source on a first fully designated 20 amp breaker or a first residential power source), may supply power to a first circuit associated with a first bank of oxygen generators, and second power cord, which receives power from a second power source (e.g., a second nominal 110 volt power source on a second fully designated 20 amp breaker or a second residential power source), may supply power to a second circuit associated with a second bank of oxygen generators. On the other hand, a single power source (e.g., a nominal 220 volt power source on a fully designated 40 amp breaker, a three-phase nominal 220 volt power source, an industrial power source, or a commercial power source) may supply power through a single power cord to supply power to a first circuit associated with a first bank of oxygen generators and to a second circuit associated with a second bank of oxygen generators.

The one or more controller devices of the control box may be configured to manage or control the pressure within the oxygen storage tank. The one or more controller devices may be configured to manage, adjust, or control the operation of the oxygen generators and the pump or compressor. The one or more controller devices may receive or react to inputs/outputs signals, signals, or communications from pressure sensors, pressure switches, pneumatic lines, other control boxes, networks, computing devices, or computer systems, or the like. The one or more controller devices may further send signals, outputs, or other communications to relays, other control boxes, other controller devices, networks, computing devices, or computer systems.

In some embodiments, the one or more controller devices may include the use of one or more relays to activate or control one or more electrical circuits associated with the oxygen generating system. For example, one or more relays may be used to control a first circuit associated with a first bank of oxygen generators and a second circuit associated with a second bank of oxygen generators. By way of example, at least one pressure switch or pressure sensor may be configured to detect a pressure and then send a signal to one or more relays; in response to the signal, the one or more relays may then switch the first and second circuit on or off. Each of the relays may be configured to control a circuit in response to a signal or by a signal. The relays may also be contactors configured for directly controlling electrical equipment. A relay may also be used to control the oil-less oxygen vacuum pump/compressor. In some implementations, the relays may include solid-state relays configured to control power circuits with no moving parts through the use of semiconductor devices to perform switching. In some implementations, the relays may include protective relays with calibrated operating characteristics and multiple operating coils used to protect electrical circuits from overload or faults.

In some implementations, the one or more relays may be located outside of the control box (such as in a remote relay and outlet box located in closer proximity to the oxygen generators).

In some implementations, the one or more controller devices may include one or more digital controllers. A digital controller may be configured to control various circuits and components of the oxygen generating system. For example, the digital controller may be communicatively coupled with one or more pressure sensors. Each of the one or more pressure sensors may sense a pressure associated with the oxygen storage tank. Each of the one or more pressure sensors may be located at, as a part of the oxygen storage tank, or on a pressure sensor line. The digital controller may receive continuous, periodic, or pressure-specific signals from the one or more pressure sensors. The signals received from the one or more pressure sensors may be electronic or wireless. When the digital controller receives the signal, the digital controller may switch one or more circuits on or off. In some implementations, switching a circuit on or off may include the use of relays incorporated into the digital controller or communicatively coupled to the digital controller. The digital controller may be configured to control whether each component of the oxygen generating system receives power or the amount of power each component receives. For example, the digital controller may control each of the following components: the oxygen compressor, a first bank of oxygen generators, a second bank of oxygen generators, individual oxygen generators of each bank of oxygen generators, and electronic sensors or gauges. The digital controller may be configured to send signals to other switches or relays located in the system for switching on or off or otherwise controlling other system components.

The digital controller may be configured to automatically manage the oxygen generating system. The digital controller may receive pressure signals from one or more pressure sensors, wherein the pressure signals are associated with a pressure of the oxygen storage tank. Based upon the pressure signal from the pressure sensor or other sensors, the digital controller may determine the pressure of the oxygen storage tank. The digital controller may then compare the determined pressure with various threshold values and determine what action to take. Each threshold value may be associated with a storage tank pressure and an action for the digital controller to take. Based upon the determined pressure of the oxygen storage tank and threshold pressure values, the digital controller may leave the system operating in its current state (e.g., status quo state), turn on or off the oxygen compressor, turn on or off the first bank of oxygen generators, turn on or off the second bank of oxygen generators, turn on or off individual oxygen generators of each bank of oxygen generators, open or close control or solenoid valves, display data, send communication signals, or variably adjust the power to each bank of oxygen generators, individual oxygen generators, or the oxygen compressor.

For example, in some embodiments the digital controller may manage an oxygen generating system in the following manner:

receiving electrical power;
receiving a first pressure signal associated with a first pressure;
determining the first pressure to be less than or equal to a first startup threshold pressure, said first pressure associated with a gaseous pressure of the oil-less tank;
providing electrical power to the oil-less air compressor;
completing a first electrical circuit, said first electrical circuit for providing electrical power to a first bank of at least one pressure swing adsorption oxygen generator;
providing electrical power to the first circuit;
receiving a second pressure signal associated with a second pressure;
determining the second pressure to be less than or equal to a second startup threshold pressure, said second pressure associated with a gaseous pressure of the oil-less tank, wherein the second startup threshold pressure is greater than the first startup threshold pressure;
completing a second electrical circuit, said second circuit for providing power to a second bank of at least one pressure swing adsorption oxygen generator;
providing electrical power to the second circuit;
receiving a third pressure signal associated with a third pressure;
determining the third pressure to be greater than or equal to a first shutoff threshold pressure, said third pressure associated with a gaseous pressure of the oil-less tank;
opening the first circuit;
cutting power to the first circuit;
receiving a fourth pressure signal associated with a fourth pressure;
determining the fourth pressure to be greater than or equal to a second shutoff threshold pressure, said fourth pressure associated with a gaseous pressure of the oil-less tank, wherein the second shutoff threshold pressure is greater than the first shutoff threshold pressure;
opening the second circuit;
cutting power to the second circuit; and
cutting power to the oil-less air compressor.

The digital controller may include a digital display configured to read out various data associated with the system, such as oxygen storage tank pressure; oxygen storage tank volume; oxygen storage tank mols (or corresponding unit of measure); oxygen compressor output pressure; oxygen compressor output flow; oxygen compressor input pressure; oxygen compressor input flow; whether the oxygen storage tank is currently gaining oxygen or losing oxygen; oxygen compressor power status (e.g., "on"/"off"/"standby"); first circuit power/first bank of oxygen generators status (e.g., "on"/"off"/"standby"); second circuit/second bank of oxygen generators power status (e.g., "on"/"off"/"standby"); first circuit voltage and amperage data; second circuit voltage and amperage data; and/or individual oxygen generator power status (e.g., "on"/"off"/"standby") of each bank of oxygen generators. The digital controller may be communicatively coupled with necessary components for obtaining and/or calculating the above various data, including voltmeters, amp meters, flow meters/sensors, pressure sensors/meters, or the like. The digital display associated with the digital controller may be configured for a user or computer system to input specific information relating to an oxygen generating system such as the capacity of the oxygen storage tank, the individual output parameters of individual oxygen generators, or the output specification of the oxygen compressor.

The digital controller may include necessary computer hardware components including one or more processors, circuit boards, memory, storage, busses, controllers, receivers, transmitters, ports, networking components, software, and/or firmware. The digital controller may be configured to wirelessly or through-wires communicate over a network with other computing devices, sensors, relays, valves (such as control valves or solenoid valves), system components, or equipment. For example, the digital controller may send signals (e.g., low voltage signals) through USB cables to relays which are configured to switch banks of oxygen generators off or on.

In some implementations, the one or more controller devices of the control box may be one or more pressure switches (e.g., two pressure switches) or may include one or more pressure switches (e.g., two pressure switches). Each of the pressure switches may be configured to control whether power is provided to a particular oxygen generator or a bank of oxygen generators. The pressure switches may respond to a pressure of the tank by either opening or closing circuits associated with a particular bank of oxygen generators. Each of the one or more pressure switches may be associated with controlling or configured to control a particular bank of oxygen generators simultaneously or synchronously. The one or more pressure switches may have adjustable pressure differentials. (The pressure differential of a pressure switch is the difference in two pressures settings of a particular pressure switch, such that the particular pressure switch "switches on (or off)" in response to a sensed first pressure and "switches off (or on)" in response to a sensed second pressure.)

In some implementations, the one or more controller devices of the control box may be one or more pneumatic controllers. The pneumatic controller may be a pneumatic logic system implemented through any of the following: one or more "and" units; one or more "or" units; one or more relay or booster units; one or more latching units; one or more timer units; one or more analog pneumatic computers (e.g., Sorteberg relays); or one or more fluidics amplifiers.

Embodiments of the invention may include or be configured to include one or more oxygen generators (also known as oxygen concentrators). The oxygen generators may comprise pressure swing adsorption oxygen generators. Each of the oxygen generators may be configured to receive power via a standard plug, plugged into a standard electrical outlet (such as a standard residentially rated and shaped electrical outlet). Each of the oxygen generators of the oxygen generating system may be a standalone oxygen generator such that each oxygen generator, independently, is configured to produce oxygen at a relatively low pressure and output flow. Because each of the oxygen generators may standalone and includes standard electrical connectivity, one or more oxygen generators of an oxygen generation system may be quickly and readily removed, exchanged, replaced, or added. Additionally, because each oxygen generator may stand alone and includes standard connectivity, particular oxygen generators of a bank or oxygen generating system may comprise non-uniform makes, models, or specifications.

There are various oxygen generators (also known as oxygen concentrators) on the market which can produce oxygen with a range of low pressures and low flow rates. An example of one manufacturer's specifications for oxygen generator models is as follows in Table 1.

TABLE 1

|  | Operating Pressure | Flow per Minute | Flow per Hour | Purity | Soft Glass | Small Boro | Medium Boro | Large Boro |
|---|---|---|---|---|---|---|---|---|
| EX-5 | 7 PSI | 5 LPM | 10.59 SCFH | 95% | Y | N | N | N |
| EX-10 | 10 PSI | 5 LPM | 10.59 SCFH | 95% | Y | Y | N | N |
| EX-15 | 15 PSI | 8 LPM | 16.94 SCFH | 95% | Y | Y | Y | N |
| H-1 | 20 PSI | 15 LPM | 31.77 SCFH | 95% | Y | Y | Y | Y |

Table 1 demonstrates that commercially available oxygen generators fail to provide the necessary pressure and/or volume required for working with large borosilicate glass ("boro") pieces with larger glass torches. Only very expensive larger systems (such as systems for hospitals and universities) provide the necessary pressure and/or volume for working with large borosilicate glass pieces with larger glass torches. While linking the oxygen output of a few of the smaller generators together increases oxygen flow output, linking the oxygen output of a few of the smaller generators together still fails to provide the required oxygen flow at the necessary pressure for working with large borosilicate glass pieces. Additionally, a nominal 110 volt/20 amp power source has a limitation of how many oxygen generators can be linked together before the power source is overloaded. For example, plugging in four oxygen generators may overload an electrical circuit rated for 20 amps.

An oxygen generating system may include or be configured to include one or more oxygen generators such that the oxygen generating system is configure to provide a sustained flow of oxygen at a pressure and flow rate suited for particular end-use purposes, such as an oxygen supply for one or more glass torches. The oxygen generators of the oxygen generating system may be configured or arranged in one or more groups (such as banks). Each group or bank of oxygen generators may include one or more oxygen generators (such as one, two, three, four, five, six, seven, or more oxygen generators). Each of the groups or banks of oxygen generators may be synchronized such that all oxygen generators of a bank of oxygen generators may be synchronously or simultaneously controlled by one or more controller devices. For example, a controller device may synchronously or simultaneously power on, power off, reduce the output, increase the output, or the like of a bank of oxygen generators. Implementations of the invention may include one or more banks of oxygen generators (such as one bank, two banks, three banks, or four banks, etc.). Furthermore, individual oxygen generators may be removed, exchanged, repaired, or replaced without causing the rest of the oxygen generator system to fail.

Some embodiments may include a toggle switch or toggle button configured for alternating the order of the first circuit and second circuit, wherein an alternated second circuit becomes the first circuit and an alternated first circuit becomes the second circuit.

Embodiments of the invention may include a pump or compressor configured to compress the generated oxygen received from the oxygen generators and pump compressed oxygen to the storage tank. The pump or compressor may include a vacuum pump compressor. The pump or compressor may be an oil-less pump or compressor configured to pump oxygen and other gasses or designed specifically to pump oxygen. The oil-less feature of the pump reduces or eliminates the possibility of combustion of oxygen and oil within the pump. The pump or compressor may be able to operate under a variety of pressures and flow rates in order to accommodate a variable number of oxygen generators (such as between one and seven oxygen generators).

The pump or compressor may be a variable speed or multi-stage pump or compressor (such as a two-stage vacuum pump). The pump or compressor must be oil-less to prevent combustion of the oxygen. The pump or compressor may be controlled by a digital controller or relay. For example, suitable pumps or compressors may be capable of and configured to compress gasses to maximum pressures ranging from at least 30 psi to in excess of 200 psi.

The pump or compressor may include an inlet and an outlet. The inlet of the pump or compressor may be configured to receive oxygen from one or more oxygen generators through tubing or piping connecting the inlet of the pump or compressor to outlets of the one or more oxygen generators. The outlet of the pump or compressor may be configured to supply oxygen to the storage tank through tubing or piping connecting the outlet of the pump or compressor to an inlet of the storage tank.

The pump or compressor may be accompanied by or enclosed by a pump housing. The pump housing may be uninsulated to prevent thermal overload; however, in some implementations, the pump housing may comprise an insulated housing (such as an internally insulated, externally insulated, semi-insulated, acoustically insulated, or non-thermally insulated housing). The pump housing may comprise a partially, mostly, or fully enclosed enclosure, such as a box. The pump housing may include vents, heat sinks, and/or one or more cooling units (such as fans) configured to minimize thermal overload. One or more sides or surfaces of the pump housing may allow for the free or forced movement of air. For example, one or more sides or surfaces of the pump housing may include grates or perforations. In other implementations of the invention, the pump housing may include noise damping elements such as noise reducing insulation. The pump housing may be contained within, attached to, adjacent to, or connected to, or comprise all or a portion of the exterior of the control box. In some implementations the pump or compressor and associated pump housing may not be located in the control box.

The storage tank may comprise a completely oil-less tank configured to hold compressed gasses, including oxygen. The storage tank may be specifically designed to hold oxygen. The storage tank may be oil-less to prevent combustion of the oxygen. Suitable storage tanks may have any of various maximum pressure capacity ratings, (such as 50 psi, 100 psi, 200 psi, or 1000 psi). The tank may include one or more inlets and one or more outlets. The tank may also include one or more ports. The storage tank may include one or more threaded reinforced bungs. The threaded reinforced bungs may be configured to accommodate one or more pressure sensors, one or more oxygen sensors, one or more back flow valves, one or more check valves, one or more oxygen inlets, one or more oxygen outlets, or the like. The output side of the oxygen storage tank may include one or more pressure regulators so that oxygen flow can be adjusted at one end-use point without resulting in a fluctuation in flow to other end-use points.

Referring to FIG. 1A, an embodiment of an oxygen generating system is depicted. In some implementations, the oxygen generating system may include a high volume and low pressure oxygen generating system, a high volume and high pressure oxygen generating system, or a high-flow output oxygen generating system. A control box 111 receives power from one or more power cords (e.g., 101 and 103). For example, a first power cord (e.g., 101) may supply power to the control box 111 from a first power source (e.g., a first nominal 110 volt, 20 amp electrical circuit), and a second power cord (e.g., 101) may supply power to the control box 111 from a second power source (e.g., a second nominal 110 volt, 20 amp electrical circuit).

The control box 111 may include one or more on/off switches (e.g., 115) and one or more ventilation fans (e.g., 113). The control box may include a pump or compressor, such as an oil-less vacuum pump compressor. The control box may include a controller device (such as a digital controller or pressure switches) and relays. The controller device may be configured to control the operation of the pump or compressor and one or more oxygen generators (e.g., 141-146). The controller device of the control box 111 may be configured to control the supply of power through one or more power supply cords 117 to the one or more oxygen generating systems (e.g., 141-146).

The one or more oxygen generators may be arranged in one or more banks, such as a first bank of oxygen generators (e.g., 141-143) and a second bank of oxygen generators (e.g., 144-146). The controller device of the control box 111 may be configured to control the supply of power to each of the one or more banks of oxygen generators (e.g., 141-143 and 144-146). By way of example, a first bank of oxygen generators (e.g., 141-143) may receive power via the control box through power supplied from a first power source to the control box through the first power cord 101; a second bank of oxygen generators (e.g., 144-146) may receive power via the control box through power supplied from a second power source to the control box through the second power cord 103.

Each bank of oxygen generators (e.g., 141-143 or 144-146) may be configured to be controlled by the controller device of the control box 111. Each bank of oxygen generators (e.g., 141-143 or 144-146) may generate oxygen and supply the oxygen to an inlet of the control box 111 through oxygen tubing, hoses, or piping (e.g., 151, 153, and 157). Oxygen tubing, hoses, or piping 151, 153 from the oxygen generators 141-146 may enter an oxygen manifold 155 to merge the oxygen lines into a single oxygen hose, tube, or pipe 157 which connects to an inlet on the control box 111.

The oxygen tubing, hose, or piping (e.g., 157) may supply oxygen from the oxygen generators through an inlet of the control box 111 to a pump or compressor of the control box 111. The pump or compressor of the control box 111 may compress the oxygen and pump the oxygen to the oxygen tank 121. The oxygen tank 121 may store the oxygen for later use. When oxygen is needed the tank may supply oxygen through oxygen tubing, a hose, or piping 127 to one or more pieces of equipment (such as a furnace, medical equipment, or veterinary equipment), an oxygen destination (such as an oxygen outlet), or an end-use device (such as a glass torch 135). For example, a glass torch 135 may receive oxygen and propane, whereby the oxygen is supplied via an oxygen line (e.g., 127) connected to the oxygen tank 121 and propane is supplied via a propane line 137 connected to a propane tank 131. The oxygen line (e.g., 127) may include one or more pressure regulating valves 125, safety release valves 123, shut-off valves, solenoid valves, control valves, or other valves. Each of the one or more pressure regulating valves (e.g., 125) may be adjusted to control the flow and/or pressure of the oxygen through an oxygen supply line (e.g., 127). In some implementations, one or more of the pressure regulating valves (e.g., 125) may be controlled by the controller device (such as a digital controller) of the control box 111.

Figure 1B:
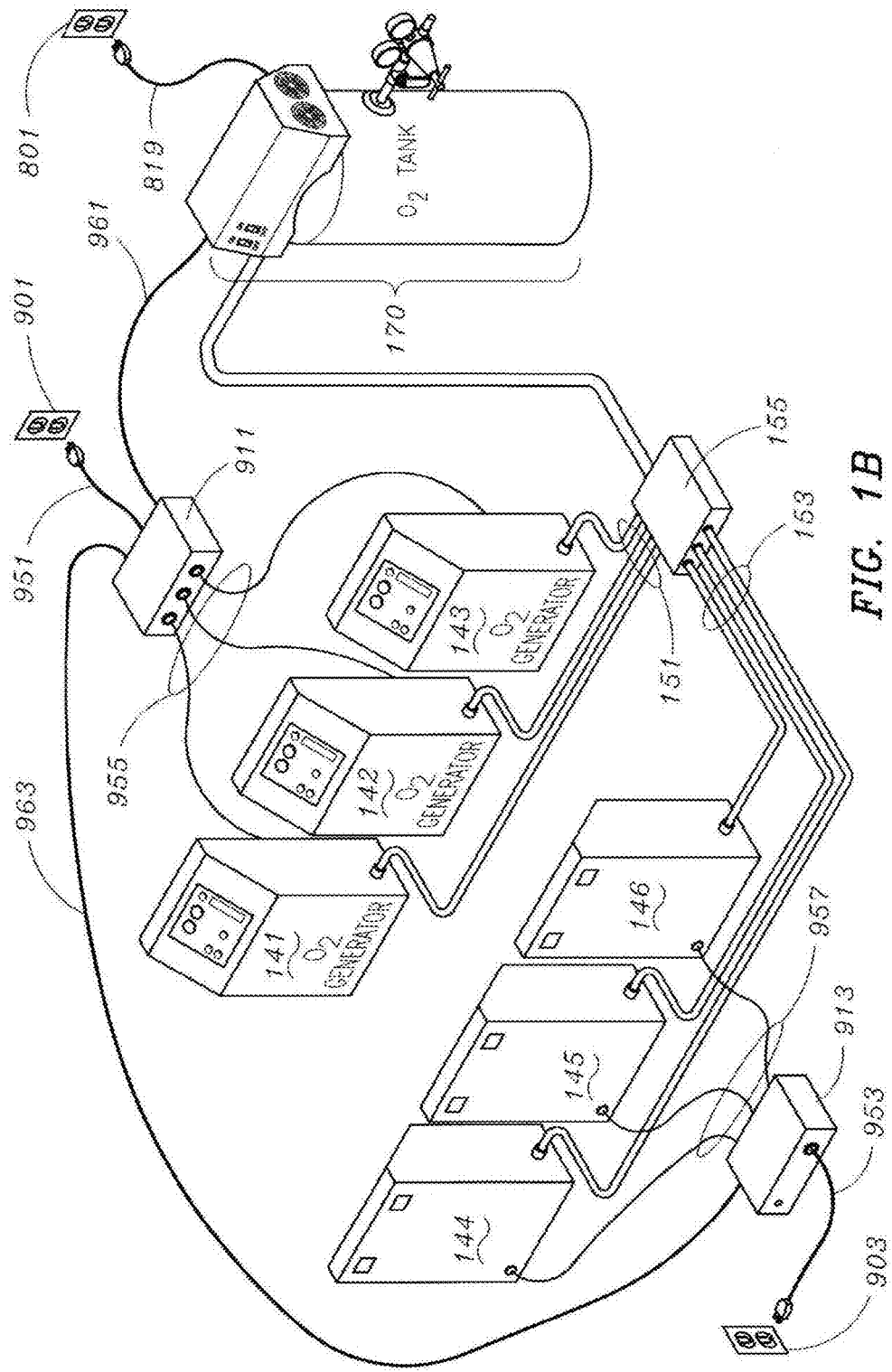
FIG. 1B shows a depiction of a further embodiment of an oxygen generating system with remote relays and outlet boxes.

Referring to FIG. 1B, an embodiment of an oxygen generating system with a main control unit and remote relays and outlet boxes is depicted. An embodiment may include a main control unit 170. The main control unit may include a control box (e.g., 110) (or the components of the control box (e.g., 110)) and an oxygen tank. For example, the main control unit may include a digital controller, an oxygen tank, and a compression system. The main control unit 170 can maintain optimized working pressures through automated digital pressure regulation. The main control unit 170 can control two or more banks of oxygen generators (141-143 and 144-146) separately to improve energy efficiency, improve precise oxygen flow control, and to reduce wear and tear on oxygen generators 141-146. The oxygen tank of the main control unit 170 may include an oil-less tank with a storage volume capacity (such as 30 gallons or 60 gallons) and may be configured to contain pressurized oxygen (such as oxygen between 40 psi and 95 psi). The weight of the main control unit may be less than 200 pounds (such as 145 pounds or 190 pounds) such that one or two people may be able to install and setup the main control unit 170 and oxygen generating system. The main control unit 170 can be connected to one or more drone units/drone control units for modular expansion of the oxygen generating system, wherein a drone unit may include an oxygen tank, a compression system, and/or relay boxes.

The main control unit 170 receives power through a power cord 819 which may receive power from a power source 801 (such as a power outlet of a nominal 110 volt, 20 amp electrical circuit). The power source 801 can be a power outlet on a 110 volt, 20 amp electrical circuit on a breaker (such as a 15 or 20 amp breaker). In some implementations, the power source 801 may include a power source on a fully dedicated breaker or shared breaker.

The one or more oxygen generators may be arranged in one or more banks, such as a first bank of oxygen generators (e.g., 141-143) and a second bank of oxygen generators (e.g., 144-146). The digital controller of the main control unit 170 may control the supply of power to each of the one or more banks of oxygen generators (e.g., 141-143 and 144-146).

Each bank of oxygen generators (e.g., 141-143 or 144-146) may be configured to be controlled by the controller device of the main control unit 170. Each bank of oxygen generators (e.g., 141-143 or 144-146) may generate oxygen and supply the oxygen to an inlet of the main control unit 170 through oxygen tubing, hoses, or piping (e.g., 151, 153, and 157). The oxygen tubing, hose, or piping (e.g., 157) may supply oxygen from the oxygen generators through an inlet of the main control unit 170 to a pump or compressor of the main control unit. The pump or compressor of the main control unit 170 may compress the oxygen and pump the oxygen to the oxygen tank of the main control unit 170. The oxygen tank of the main control unit 170 may store the oxygen for later use. When oxygen is needed the tank may supply oxygen through oxygen tubing, a hose, or piping to one or more pieces of equipment (such as a furnace, medical equipment, or veterinary equipment), an oxygen destination (such as an oxygen outlet), or an end-use device (such as a glass torch 135).

The first remote relay and outlet box 911 may be located away from the oxygen tank of the main control unit 170. The first remote relay and outlet box 911 may include an electrical line 951 connected to a power source 901; a first relay connected to the electrical line 951, communication cable or wire 961, 963, and power outlets for each oxygen generator; and the power outlets for the oxygen generators 141-143. For example, the power source 901 may be a 110 volt, 20 amp power source on a fully designated 20 amp breaker. Power cords 955 of the oxygen generators 141-143 may be plugged into power outlets of the remote relay and outlet box 911. The first relay 833 may be configured to receive power from the power source 901 via the electrical line 951, controllably provide power to power outlets for oxygen generators 141-143, and receive and/or send signals from or to the digital controller of the main control unit 170 via the communication cable or wire 961. The first remote relay and outlet box may further allow signals to be passed between a second remote relay and outlet box 913 and the digital controller of the main control unit 170 via the communication cable or wire 963.

The second remote relay and outlet box 913 may be located away from the oxygen tank of the main control unit 170. The second remote relay and outlet box 913 may include an electrical line 953 connected to a power source 903; a first relay connected to the electrical line 953, communication cable or wire 963, and power outlets for each oxygen generator 144-146; and the power outlets for the oxygen generators 144-146. For example, the power source 903 may be a 110 volt, 20 amp power source on a fully designated 20 amp breaker. Power cords 957 of the oxygen generators 141-143 may be plugged into power outlets of the remote relay and outlet box 913. The first relay 833 may be configured to receive power from the power source 901 via the electrical line 953, controllably provide power to power outlets for oxygen generators 141-143, and receive and/or send signals from or to the digital controller of the main control unit 170 via the communication cable or wire 961.

Embodiments of the present disclosure can require a minimum of three fully dedicated 15 amp breakers or two fully dedicated 20 amp breakers. For example, power sources 801, 901, and 903 may each be connected electrical circuits on a fully dedicated 15 amp breaker; or by further example, power sources 801 and 901 may be connected to an electrical circuit on a fully dedicated 20 amp breaker, and power source 903 may be connected to an electrical circuit on a fully dedicated 15 amp or 20 amp breaker.

Figure 2:
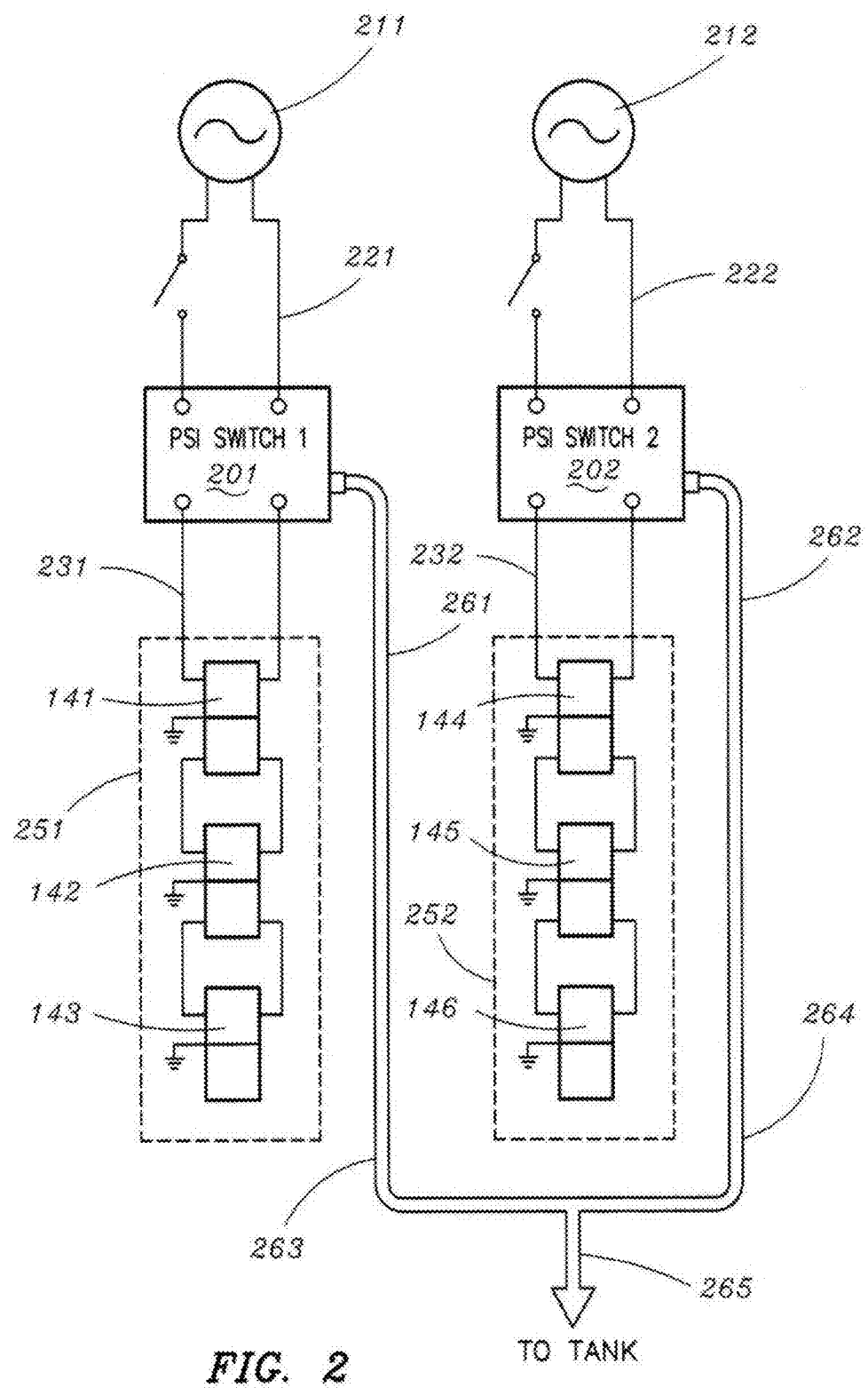
FIG. 2 shows a diagram of a portion of an embodiment of the invention including two pressure switches.

Referring to FIG. 2, a diagram of a portion of an embodiment of the invention including pressure switches is depicted. A first power source (such as a nominal 110 volt, 20 amp power source on a first fully designated 20 amp breaker) 211 provides power through a first circuit 221 to a first pressure switch 201. A second power source (such as a nominal 110 volt, 20 amp power source on a second fully designated 20 amp breaker) 212 provides power through a second circuit 222 to a second pressure switch 202. The first pressure switch 201 may receive power from the first power source 211 via the first circuit 221. The first pressure switch 201 may include a gas inlet port whereby the first pressure switch senses the pressure of the gas (e.g., oxygen) which is connected to the gas inlet port supplied from an oxygen line, piping, hose, or tubing 261 connected to the oxygen tank. The first pressure switch 201 may be configured to provide power to a first bank of oxygen generators 141-143 via an electrical circuit 231 connected to the first bank of oxygen generators 141-143 and the first pressure switch 201. The first pressure switch 201 may be configured to provide power to the first bank of oxygen generators when the pressure switch senses an oxygen pressure that is less than or equal to a first threshold pressure (e.g., 35 psi). The first pressure switch 201 may also be configured to turn off or cease to provide power when the first pressure switch 201 senses an oxygen pressure that is more than or equal to a second threshold power (e.g., 80 psi).

The second pressure switch 202 may receive power from the first power source 212 via the second circuit 222. The second pressure switch 202 may include a gas inlet port whereby the second pressure switch 202 senses the pressure of the gas (e.g., oxygen) which is connected to the gas inlet port supplied from an oxygen line, piping, hose, or tubing 262 connected to the oxygen tank. The second pressure switch 202 may be configured to provide power to a second bank of oxygen generators 144-146 via an electrical circuit 232 connected the second bank of oxygen generators 144-146 and the second pressure switch 202. The second pressure switch 202 may be configured to provide power to the second bank of oxygen generators when the pressure switch senses an oxygen pressure that is less than or equal to a third threshold pressure (e.g., 32 psi). The second pressure switch 202 may also be configured to turn off or cease to provide power when the second pressure switch 202 senses an oxygen pressure that is more than or equal to a second threshold pressure (e.g., 77 psi).

The first pressure switch may be configured to turn on the pump or compressor when the first bank of oxygen generators is turned on; in some implementations, the second pressure switch may be configured to turn on the pump or compressor when the second bank of oxygen generators is turned on. Similarly, the second pressure switch may be configured to turn off the pump or compressor when the second bank of oxygen generators is turned off; in some implementations, the first pressure switch may be configured to turn off the pump or compressor when the first bank of oxygen generators is turned off.

Figure 3:
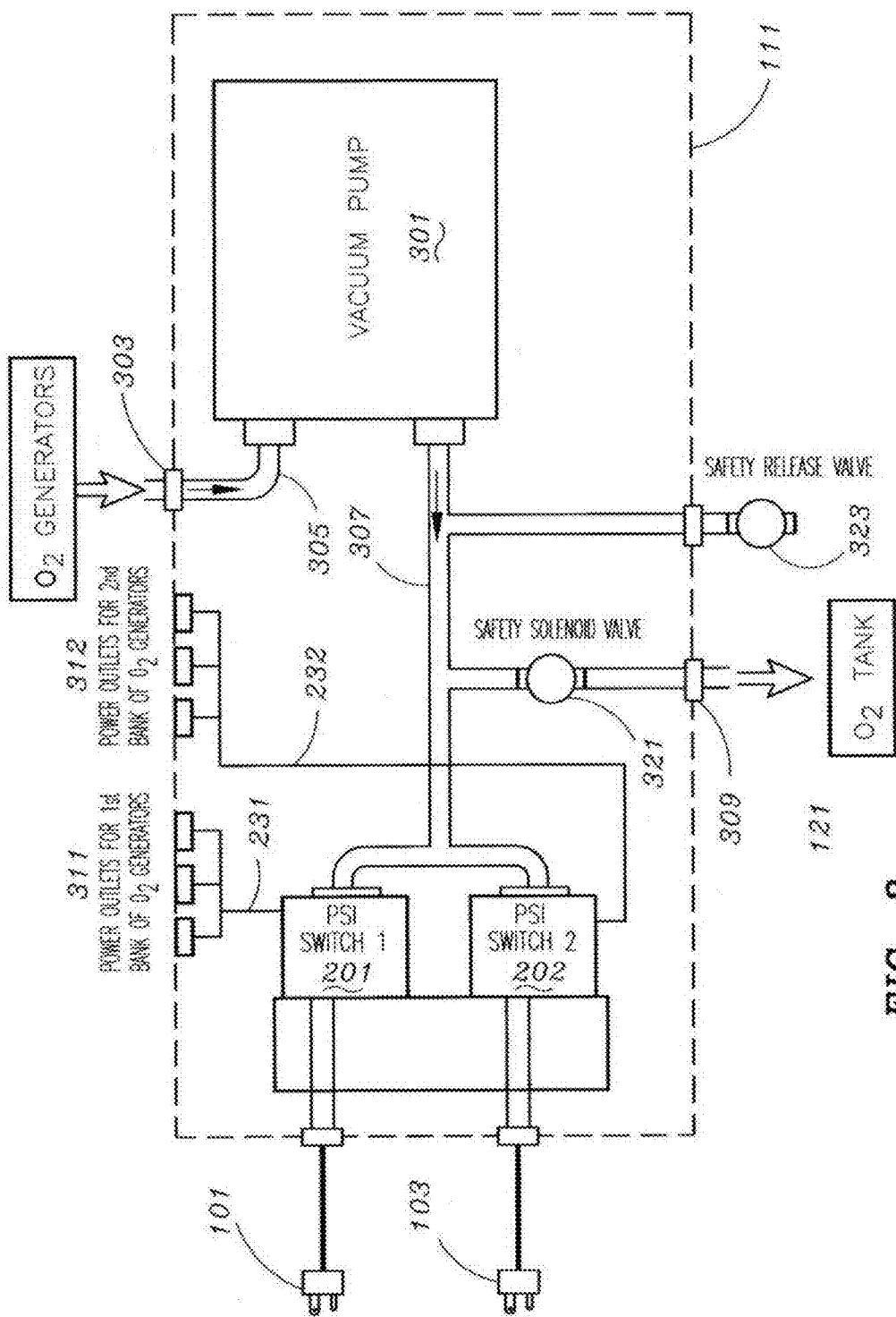
FIG. 3 shows a diagram of a portion of an embodiment of the invention including a control box with two pressure switches.

Referring to FIG. 3, a diagram of a control box 111 of an embodiment of the invention is depicted. The control box 111 may include a pump or compressor (e.g. a vacuum pump 301); pressure switches (e.g., 201, 202); power outlets 311 for a first bank of oxygen generators; power outlets 312 for a second bank of oxygen generators; a first power cord 101 for providing power to a first pressure switch; a second power cord 103 for providing power to a second pressure switch; one or more safety solenoid valves (e.g., 321); one or more safety release valves (e.g., 323); one or more oxygen inlet ports (e.g., 303); one or more oxygen outlet ports (e.g., 309); electrical lines 231 connected between the power outlets 311 for the first bank of oxygen generators and the first pressure switch 201; electrical lines 232 connected between the power outlets 312 for the second bank of oxygen generators and the second pressure switch 202; electrical lines (not shown) connecting the pump or compressor (e.g., 301) to one or more of the pressure switches (e.g., 201, 202) or a power source; oxygen tubing, piping, or hose 305 connecting the oxygen inlet port (e.g., 303) to the pump or compressor (e.g., 301); and/or oxygen tubing, piping, or hose 307 connecting the pump or compressor (e.g., 301) to the oxygen outlet port (e.g., 303), the first pressure switch 201, the second pressure switch 202, the safety release valve 323, and/or the safety solenoid valve 321.

Figure 4:
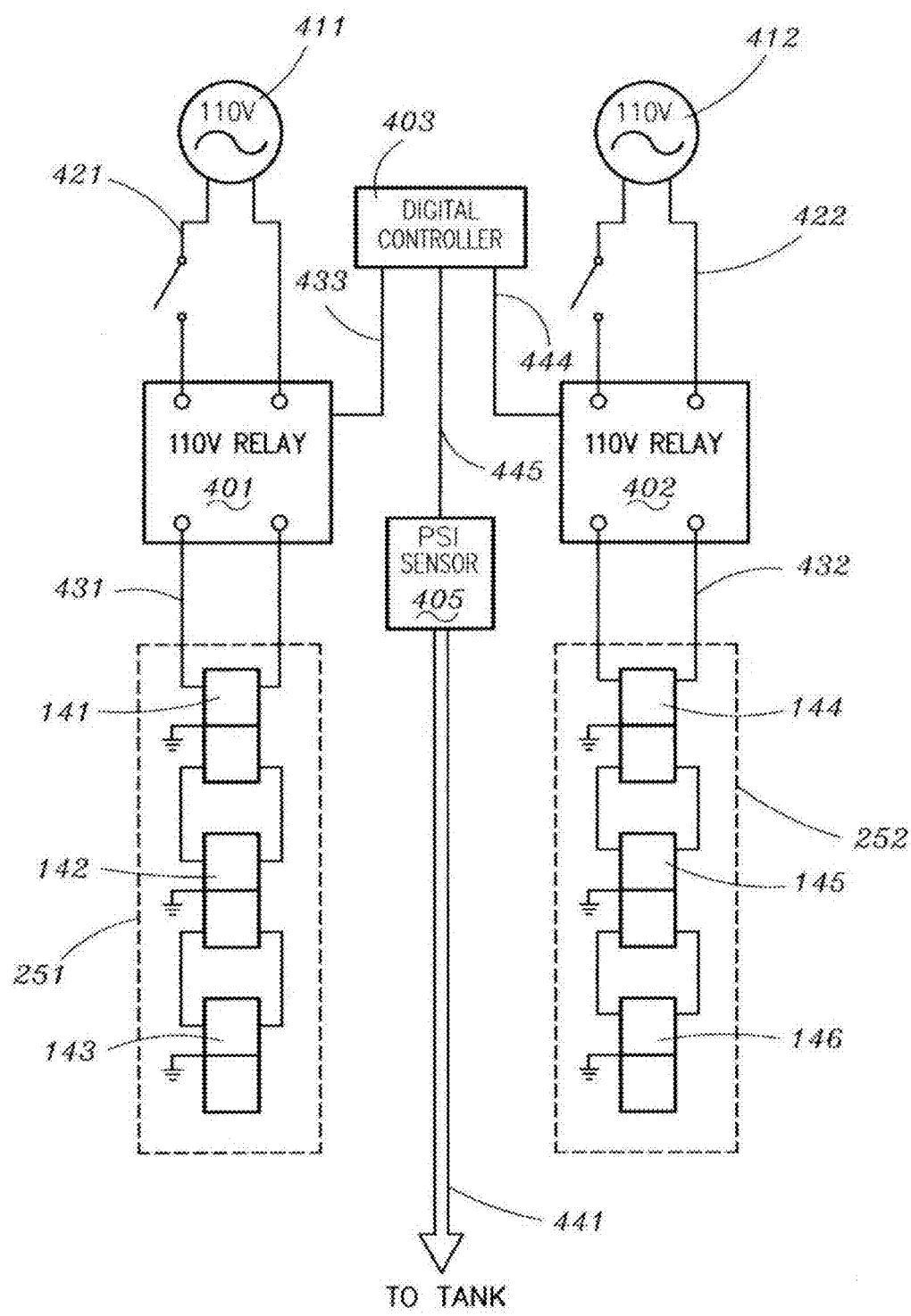
FIG. 4 shows a diagram of a portion of an embodiment of the invention including a digital controller, two relays, and a pressure sensor.

Referring to FIG. 4, a diagram of a portion of an embodiment of the invention including a digital controller 403 is depicted. A first power source (such as a nominal 110 volt, 20 amp power source connected to a first fully designated 20 amp breaker) 411 provides power through a first circuit 421 to a first relay 401. A second power source (such as a nominal 110 volt, 20 amp power source connected to a second fully designated 20 amp breaker) 412 provides power through a second circuit 422 to a second relay 402.

A digital controller 403 may be communicatively connected to the first relay 401, the second relay 402, and/or one or more pressure sensors (e.g., 405). The digital controller 403 may receive signals from a pressure sensor 405, whereby each of the signals indicates a pressure associated with the system (such as a pressure associated with an oxygen storage tank connected to the pressure sensor via oxygen tubing, hoses, or piping (e.g., 441)).

In response to signals received from one or more pressure sensors (e.g., 405), the digital controller 403 may control one or more of the first relay 401 or the second relay 402. As a first example, the pressure sensor 405 may sense a first pressure. The pressure sensor 405 may then send a signal corresponding to the first sensed pressure to the digital controller 403. The digital controller 403 may determine that the first pressure is less than or equal to a first threshold pressure (e.g., 35 psi). Based upon the signal corresponding to the first pressure being less than or equal to a first threshold pressure, the digital controller 403 may send a signal to the first relay 401 to provide power to the first bank 251 of oxygen generators 141-143. Upon receiving the signal to provide power from the digital controller 403, the first relay 401 may switch the power on or provide power to the first bank 251 of oxygen generators 141-143.

As a second example, the pressure sensor 405 may sense a second pressure. The pressure sensor 405 may then send a signal corresponding to the second sensed pressure to the digital controller 403. The digital controller 403 may determine that the second pressure is greater than or equal to a second threshold pressure (e.g., 80 psi). Based upon the signal corresponding to the second pressure being greater than or equal to a second threshold pressure, the digital controller 403 may send a signal to the first relay 401 to cease to provide power to the first bank 251 of oxygen generators 141-143. Upon receiving the signal to cease to provide power from the digital controller 403, the first relay 401 may switch the power off or cease to provide power to the first bank 251 of oxygen generators 141-143.

As a third example, the pressure sensor 405 may sense a third pressure. The pressure sensor 405 may then send a signal corresponding to the third sensed pressure to the digital controller 403. The digital controller 403 may determine that the third pressure is less than or equal to a third threshold pressure (e.g., 32 psi). Based upon the signal corresponding to the third pressure being less than or equal to a third threshold pressure, the digital controller 403 may send a signal to the second relay 402 to provide power to the second bank 252 of oxygen generators 144-146. Upon receiving the signal to provide power from the digital controller 403, the second relay 402 may switch the power on or provide power to the second bank 252 of oxygen generators 144-146.

As a fourth example, the pressure sensor 405 may sense a fourth pressure. The pressure sensor 405 may then send a signal corresponding to the fourth sensed pressure to the digital controller 403. The digital controller 403 may determine that the fourth pressure is greater than or equal to a fourth threshold pressure (e.g., 77 psi). Based upon the signal corresponding to the fourth pressure being greater than or equal to a fourth threshold pressure, the digital controller 403 may send a signal to the second relay 401 to cease to provide power to the second bank 252 of oxygen generators 144-146. Upon receiving the signal to cease to provide power from the digital controller 403, the second relay 402 may switch the power off or cease to provide power to the second bank 252 of oxygen generators 144-146.

The digital controller 403 may be configured to operably control the relays (e.g., 401, 402), and thus, the oxygen generators (e.g., 141-146). In some implementations, the digital controller's ability to control the oxygen generators (141-146) may include the ability to turn on individual oxygen generators; turn off individual oxygen generators; variably control the power supplied to all, some, or individual oxygen generators; variably control the speed or output of all, some, or individual oxygen generators; or the like. The digital controller 403 may be further configured to control the operation of a pump or compressor contained within the control box. For example, the digital controller 403 may coordinate the control of the pump or compressor with the operation of the oxygen generators (e.g., 141-146) such that if any of the oxygen generators (e.g., 141-146) are currently "on" or receiving power, the digital controller 403 will control the pump or compressor to also be "on" or receiving power.

Figure 5:
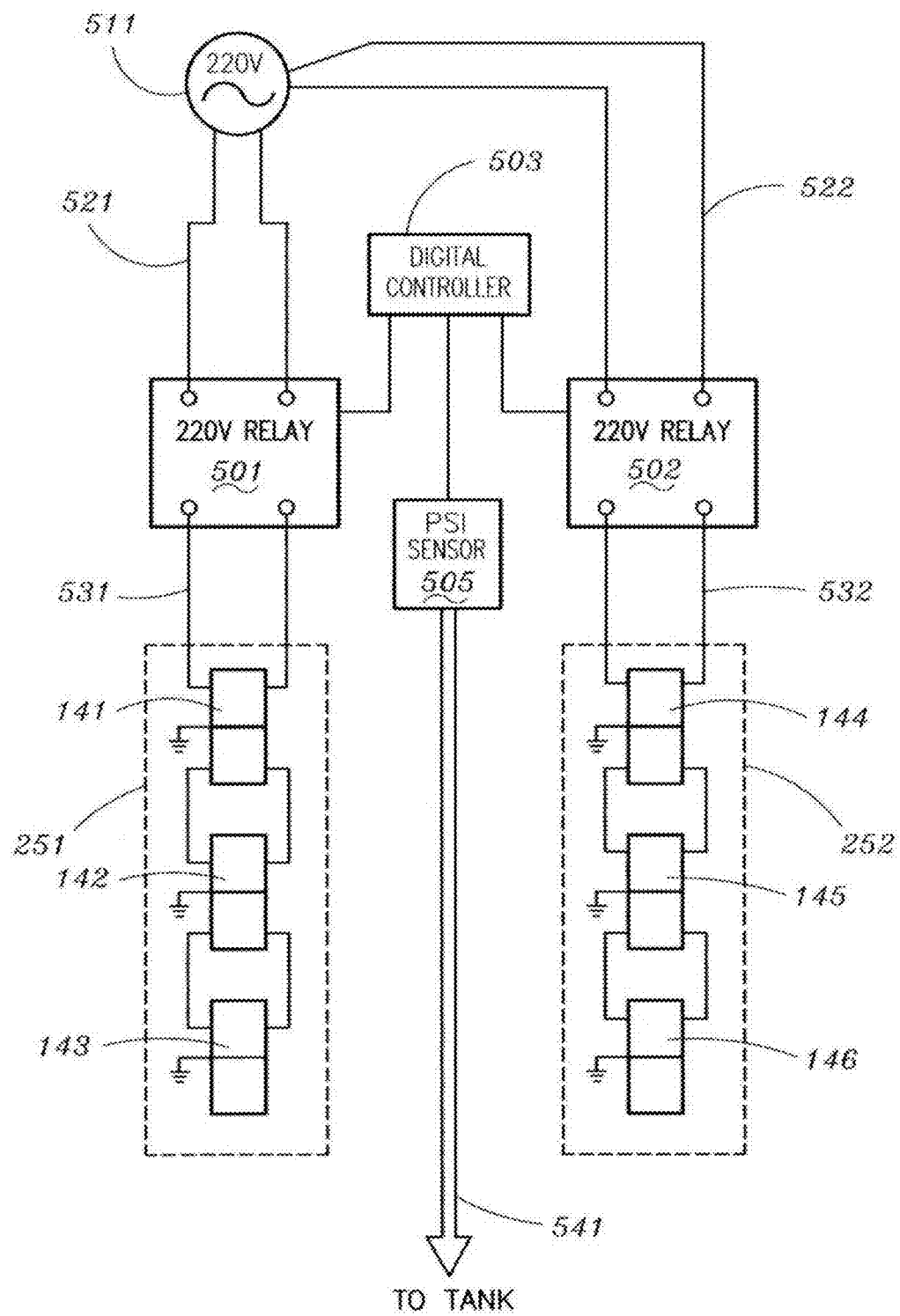
FIG. 5 shows a diagram of a portion of an embodiment of the invention including a digital controller, two relays, and a pressure sensor.

Referring to FIG. 5, a diagram of a portion of an embodiment of the invention including a digital controller 503 is depicted. A power source (such as a nominal 220 volt/40 amp) power source connected to a fully designated 40 amp breaker or three-phase nominal 220 volt power source) 511 provides power through a first circuit 521 to a first relay 501. The power source 511 provides power through a second circuit 522 to a second relay 502.

A digital controller 503 may be communicatively connected to the first relay 501, the second relay 502, and/or one or more pressure sensors (e.g., 505). The digital controller 503 may receive signals from a pressure sensor 505, whereby each of the signals indicates a pressure associated with the system (such as a pressure associated with an oxygen storage tank connected to the pressure sensor via oxygen tubing, hoses, or piping (e.g., 541)).

In response to signals received from one or more pressure sensors (e.g., 505), the digital controller 503 may control one or more of the first relay 501 or the second relay 502. As a first example, the pressure sensor 505 may sense a first pressure. The pressure sensor 405 may then send a signal corresponding to the first sensed pressure to the digital controller 503. The digital controller 503 may determine that the first pressure is less than or equal to a first threshold pressure (e.g., 35 psi). Based upon the signal corresponding to the first pressure being less than or equal to a first threshold pressure, the digital controller 503 may send a signal to the first relay 501 to provide power to the first bank 251 of oxygen generators 141-143. Upon receiving the signal to provide power from the digital controller 503, the first relay 501 may switch the power on or provide power to the first bank 251 of oxygen generators 141-143.

As a second example, the pressure sensor 505 may sense a second pressure. The pressure sensor 505 may then send a signal corresponding to the second sensed pressure to the digital controller 503. The digital controller 503 may determine that the second pressure is greater than or equal to a second threshold pressure (e.g., 80 psi). Based upon the signal corresponding to the second pressure being greater than or equal to a second threshold pressure, the digital controller 403 may send a signal to the first relay 501 to cease to provide power to the first bank 251 of oxygen generators 141-143. Upon receiving the signal to cease to provide power from the digital controller 503, the first relay 501 may switch the power off or cease to provide power to the first bank 251 of oxygen generators 141-143.

As a third example, the pressure sensor 505 may sense a third pressure. The pressure sensor 505 may then send a signal corresponding to the third sensed pressure to the digital controller 503. The digital controller 503 may determine that the third pressure is less than or equal to a third threshold pressure (e.g., 32 psi). Based upon the signal corresponding to the third pressure being less than or equal to a third threshold pressure, the digital controller 503 may send a signal to the second relay 502 to provide power to the second bank 252 of oxygen generators 144-146. Upon receiving the signal to provide power from the digital controller 503, the second relay 502 may switch the power on or provide power to the second bank 252 of oxygen generators 144-146.

As a fourth example, the pressure sensor 505 may sense a fourth pressure. The pressure sensor 505 may then send a signal corresponding to the fourth sensed pressure to the digital controller 503. The digital controller 503 may determine that the fourth pressure is greater than or equal to a fourth threshold pressure (e.g., 77 psi). Based upon the signal corresponding to the fourth pressure being greater than or equal to a fourth threshold pressure, the digital controller 503 may send a signal to the second relay 501 to cease to provide power to the second bank 252 of oxygen generators 144-146. Upon receiving the signal to cease to provide power from the digital controller 503, the second relay 502 may switch the power off or cease to provide power to the second bank 252 of oxygen generators 144-146.

The digital controller 503 may be configured to operably control the relays (e.g., 501, 502), and thus, the oxygen generators (e.g., 141-146). In some implementations, the digital controller's ability to control the oxygen generators (141-146) may include the ability to turn on individual oxygen generators; turn off individual oxygen generators; variably control the power supplied to all, some, or individual oxygen generators; variably control the speed or output of all, some, or individual oxygen generators; or the like. The digital controller 503 may be further configured to control the operation of a pump or compressor contained within the control box. For example, the digital controller 503 may coordinate the control of the pump or compressor with the operation of the oxygen generators (e.g., 141-146) such that if any of the oxygen generators (e.g., 141-146) are currently "on" or receiving power, the digital controller 503 will control the pump or compressor to also be "on" or receiving power.

Figure 6:
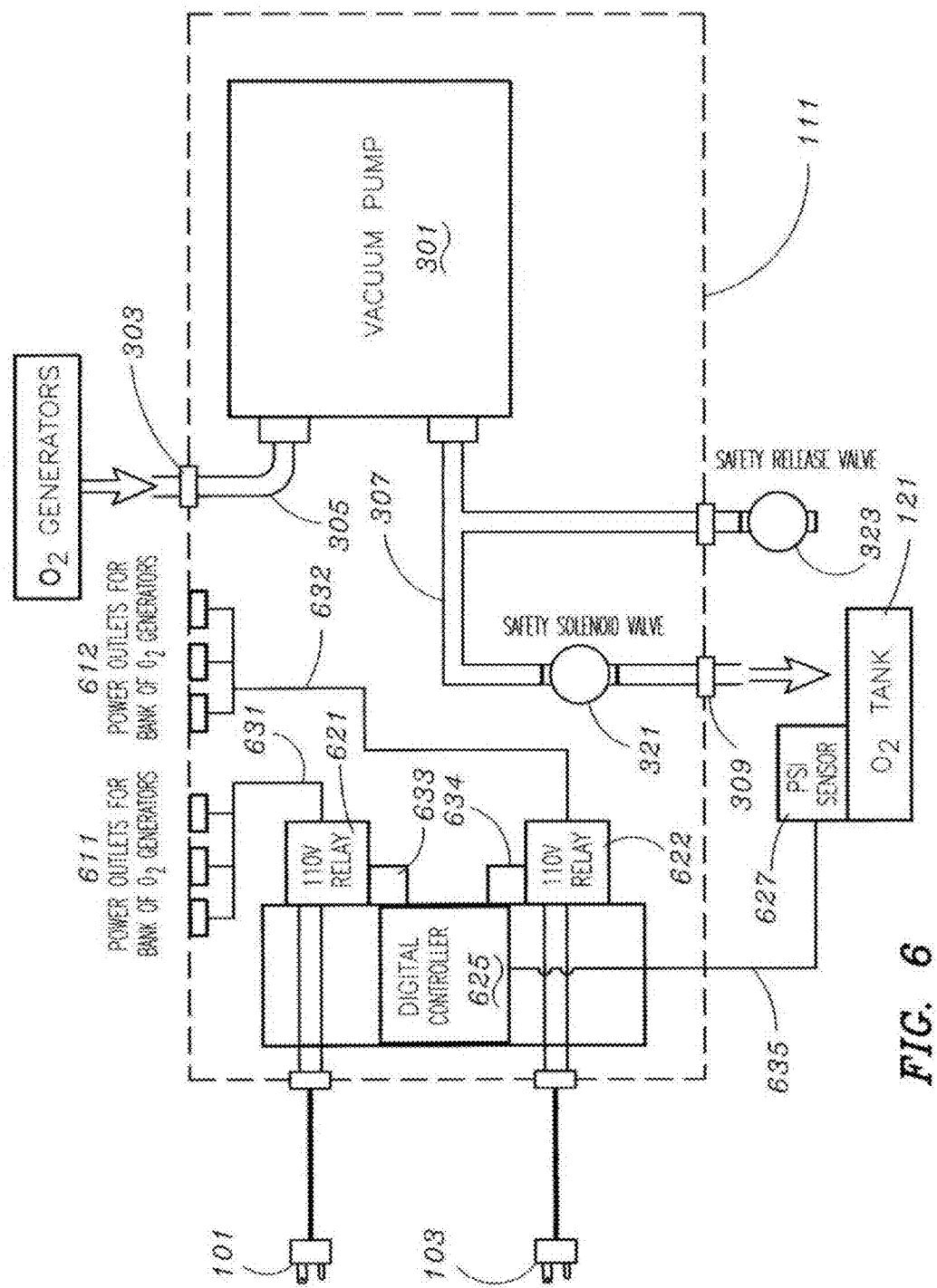
FIG. 6 shows a diagram of a portion of an embodiment of the invention including a control box with a digital controller and relays.

Referring to FIG. 6, a diagram of a control box 111 of an embodiment of the invention is depicted. The control box 111 may include a pump or compressor (e.g. a vacuum pump 301); a digital controller 625; power outlets 611 for a first bank of oxygen generators; power outlets 612 for a second bank of oxygen generators; a first power cord 101 for providing power to a first relay 621; a second power cord 103 for providing power to a second relay 622; one or more safety solenoid valves (e.g., 321); one or more safety release valves (e.g., 323); one or more oxygen inlet ports (e.g., 303); one or more oxygen outlet ports (e.g., 309); electrical lines 631 connected between the power outlets 611 for the first bank of oxygen generators and the first relay 621; electrical lines 632 connected between the power outlets 612 for the second bank of oxygen generators and the second relay 622; cables or wiring 633 connecting the first relay 621 to the digital controller 625; cables or wiring 634 connecting the second relay 622 to the digital controller 625; cables or wiring 635 connecting the digital controller 625 to a pressure sensor 627, which is configured to sense the pressure of an oxygen tank 121; electrical lines (not shown) connecting the pump or compressor (e.g., 301) to one or more of relays (e.g., 621, 622) or a power source; oxygen tubing, piping, or hose 305 connecting the oxygen inlet port (e.g., 303) to the pump or compressor (e.g., 301); and/or oxygen tubing, piping, or hose 307 connecting the pump or compressor (e.g., 301) to the oxygen outlet port (e.g., 303), the safety release valve 323, and/or the safety solenoid valve 321.

Figure 7:
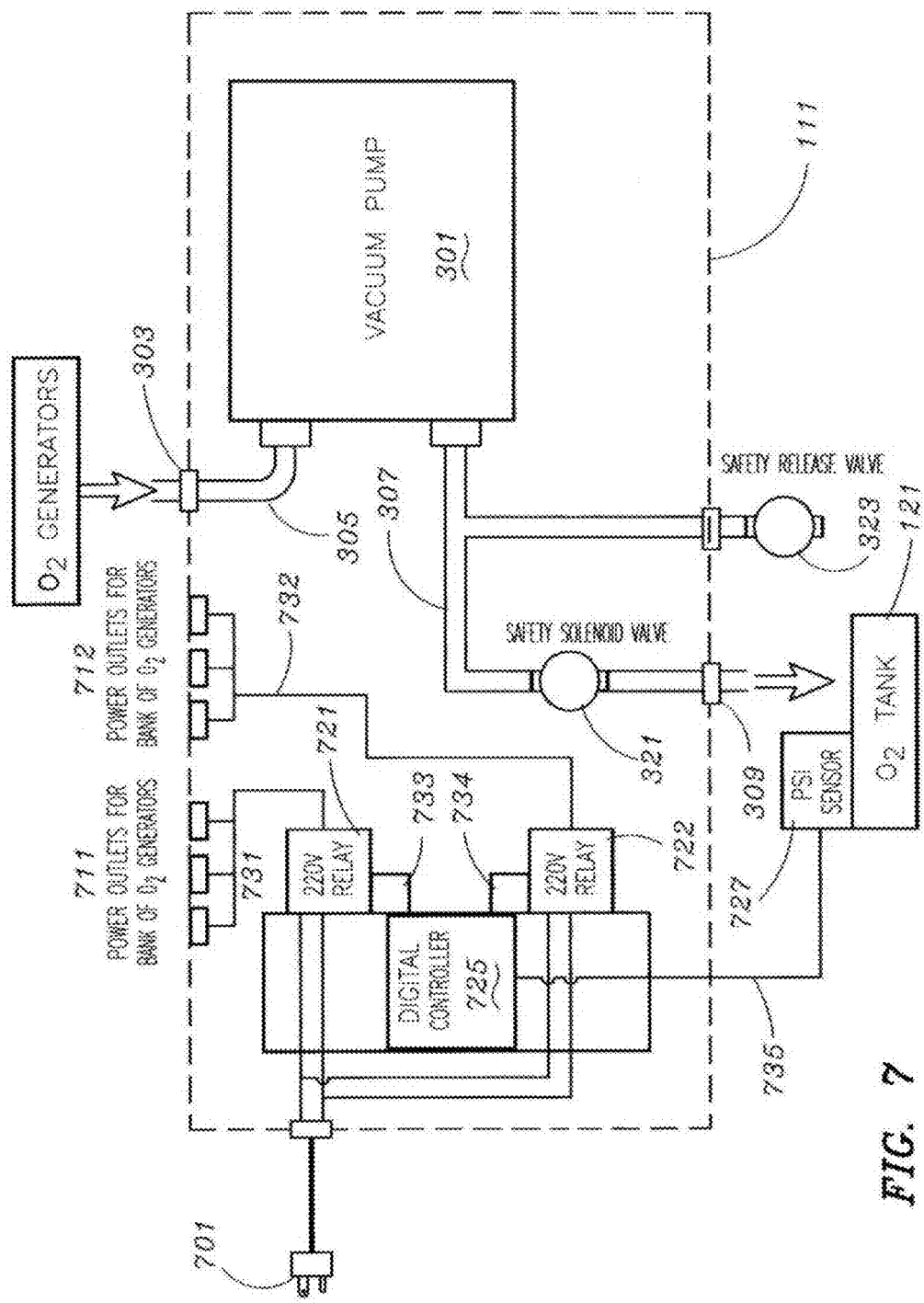
FIG. 7 shows a diagram of a portion of an embodiment of the invention including a control box with a digital controller and relays.

Referring to FIG. 7, a diagram of a control box 111 of an embodiment of the invention is depicted. The control box 111 may include a pump or compressor (e.g. a vacuum pump 301); a digital controller 725; power outlets 711 for a first bank of oxygen generators; power outlets 712 for a second bank of oxygen generators; a first power cord 701 for providing power to a first relay 721 and to a second relay 722; one or more safety solenoid valves (e.g., 321); one or more safety release valves (e.g., 323); one or more oxygen inlet ports (e.g., 303); one or more oxygen outlet ports (e.g., 309); electrical lines 731 connected between the power outlets 711 for the first bank of oxygen generators and the first relay 721; electrical lines 732 connected between the power outlets 712 for the second bank of oxygen generators and the second relay 722; cables or wiring 733 connecting the first relay 721 to the digital controller 725; cables or wiring 734 connecting the second relay 722 to the digital controller 725; cables or wiring 735 connecting the digital controller 725 to a pressure sensor 727, which is configured to sense the pressure of an oxygen tank 121; electrical lines (not shown) connecting the pump or compressor (e.g., 301) to one or more of relays (e.g., 721, 722) or a power source; oxygen tubing, piping, or hose 305 connecting the oxygen inlet port (e.g., 303) to the pump or compressor (e.g., 301); and/or oxygen tubing, piping, or hose 307 connecting the pump or compressor (e.g., 301) to the oxygen outlet port (e.g., 303), the safety release valve 323, and/or the safety solenoid valve 321.

Figure 8:
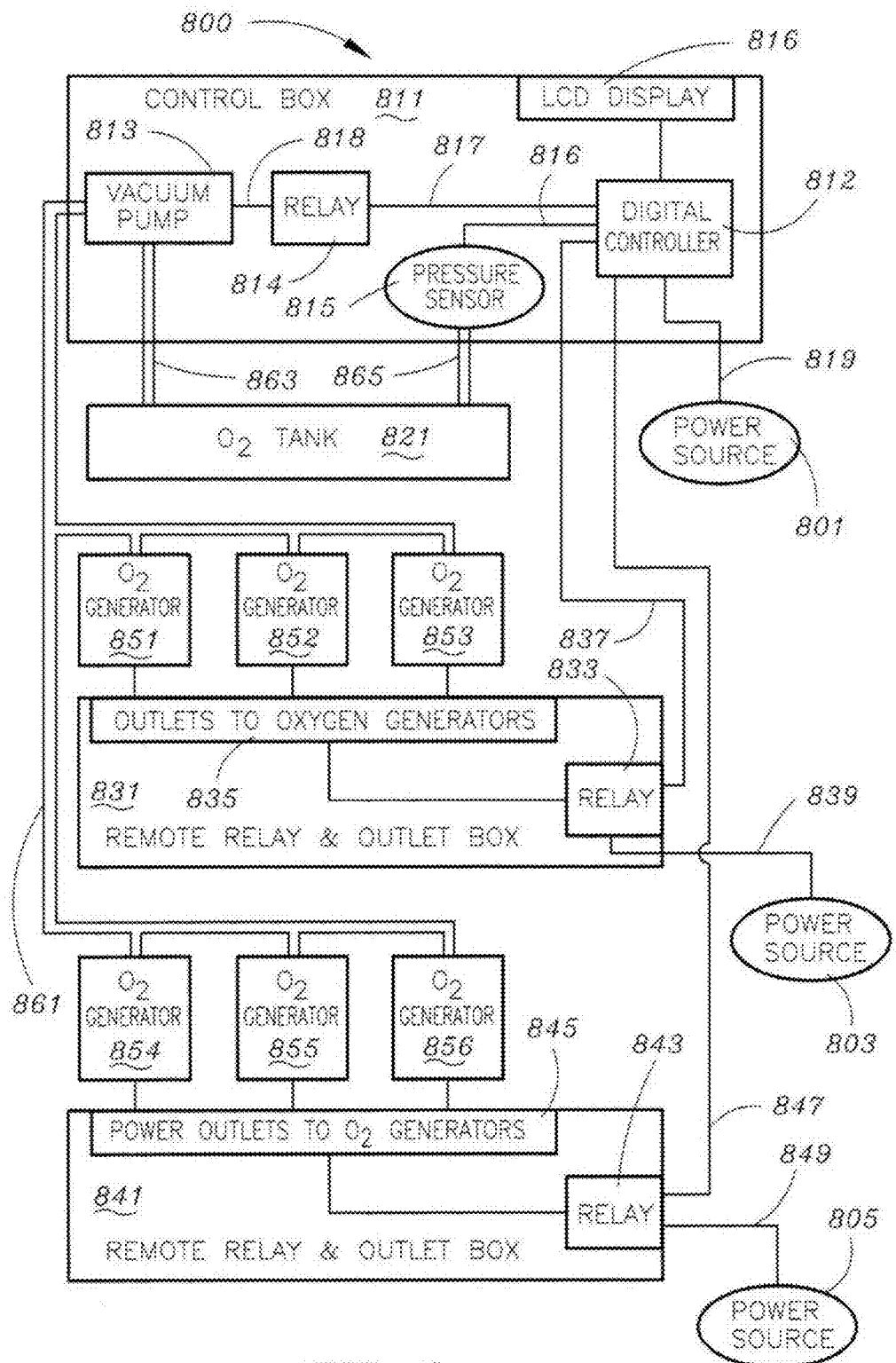
FIG. 8 shows a diagram of an embodiment of an oxygen generating system with remote relay and outlet boxes.

Referring to FIG. 8, a diagram of an embodiment of an oxygen generating system 800 is depicted. The oxygen generating system 800 may include a control box 811; an oxygen tank 821; oxygen generators 851-856; a first remote relay and outlet box 831; a second remote relay and outlet box 841; power sources (e.g., 801, 803, 805); oxygen piping, hoses, or tubing (e.g., 861, 863, 865); electrical lines (e.g., 819, 839, 849); cables or wiring (e.g., 837, 847), or the like.

Still referring to FIG. 8, the control box 811 may include a pump or compressor (e.g., 813) (such as a vacuum pump); one or more relays (e.g., 814); one or more controller devices (e.g., 812) (such as one or more digital controllers); one or more pressure sensors (e.g., 815); one or more displays (e.g., 816); an electrical line 819 connecting a first power source 801 to the control box and the digital controller 812; electrical lines, cables, or wires 817 connecting the digital controller 812 to a relay 814; electrical lines, cables, or wires 818 connecting the relay 814 to the vacuum pump 813; cables, or wires 816 connecting the digital controller 812 to the pressure sensor 815; oxygen piping, hoses, or tubing 861 connecting the vacuum pump 813 to the oxygen generators 851-856; oxygen piping, hoses, or tubing 863 connecting the vacuum pump 813 to the oxygen tank 821; oxygen piping, hoses, or tubing 865 connecting the pressure sensor 815 to the oxygen tank 821; cables or wiring 837 connecting the digital controller 812 to a first relay 833 of the first remote relay and outlet box 831; cables or wiring 847 connecting the digital controller 812 to a second relay 843 of the second remote relay and outlet box 841, or the like.

The one or more displays (e.g., 816) may be, for example, an LCD ("liquid crystal diode") display or an LED ("light emitting diode") display. The one or more displays (e.g., 816) may include a touch-screen user interface or be configured as a touch-screen display. The one or more displays (e.g., 816) may be communicatively coupled to the digital controller 812, one or more other digital controllers, one or more computing devices, one or more computer systems, one or more computer networks, one or more wired or wireless networks, or the like.

Further referring to FIG. 8, the first remote relay and outlet box 831 may be located away from the oxygen tank 821 and the control box 811. The first remote relay and outlet box 831 may include an electrical line 839 connected to a power source 803; a first relay connected to the electrical line 839, the cable or wire 837, and an electrical line to power outlets 835; and the power outlets 835 for the oxygen generators (e.g., 851-853). For example, the power source 803 may be a 110 volt, 20 amp power source on a fully designated 20 amp breaker. The first relay 833 may be configured to receive power from the power source 803 via the electrical line 839, controllably provide power to power outlets 835 for oxygen generators (e.g., 851-853), and receive and/or send signals from or to the digital controller 812 via a cable or wire 837.

The second remote relay and outlet box 841 may be located away from the oxygen tank 821 and the control box 811. The second remote relay and outlet box 841 may include an electrical line 849 connected to a power source 805; a second relay 843 connected to the electrical line 849, the cable or wire 847, and an electrical line to power outlets 845; and the power outlets 845 for the oxygen generators (e.g., 854-856). For example, the power source 805 may be a 110 volt, 20 amp power source on a fully designated 20 amp breaker. The second relay 843 may be configured to receive power from the power source 805 via the electrical line 839, controllably provide power to power outlets 835 for oxygen generators (e.g., 851-853), and receive and/or send signals from or to the digital controller 812 via a cable or wire 837.

The nonproximity of the remote relay and outlet boxes (e.g., 831, 841) to the control box 811 may be safer because the first relay 833, the second relay 843, power outlets to the oxygen generators (e.g., 835, 845), and electrical lines (e.g., 839,849) associated with powering the oxygen generators (e.g., 851-856) may be located a safer distance away from the compressed oxygen lines (e.g., 863, 865) and the oxygen tank 821 near the control box 811. Additionally, the first remote relay and outlet box (e.g., 831) may be located in closer to proximity to the first power source 831 connected to a fully designated breaker (such as a first 110 volt, 20 amp power source connected to a first fully designated 20 amp breaker); and the second remote relay and outlet box (e.g., 841) may be located in closer proximity to the second power source 841 connected to a second fully designated breaker (such as a second 110 volt, 20 amp power source connected to a second fully designated 20 amp breaker).

Figure 9:
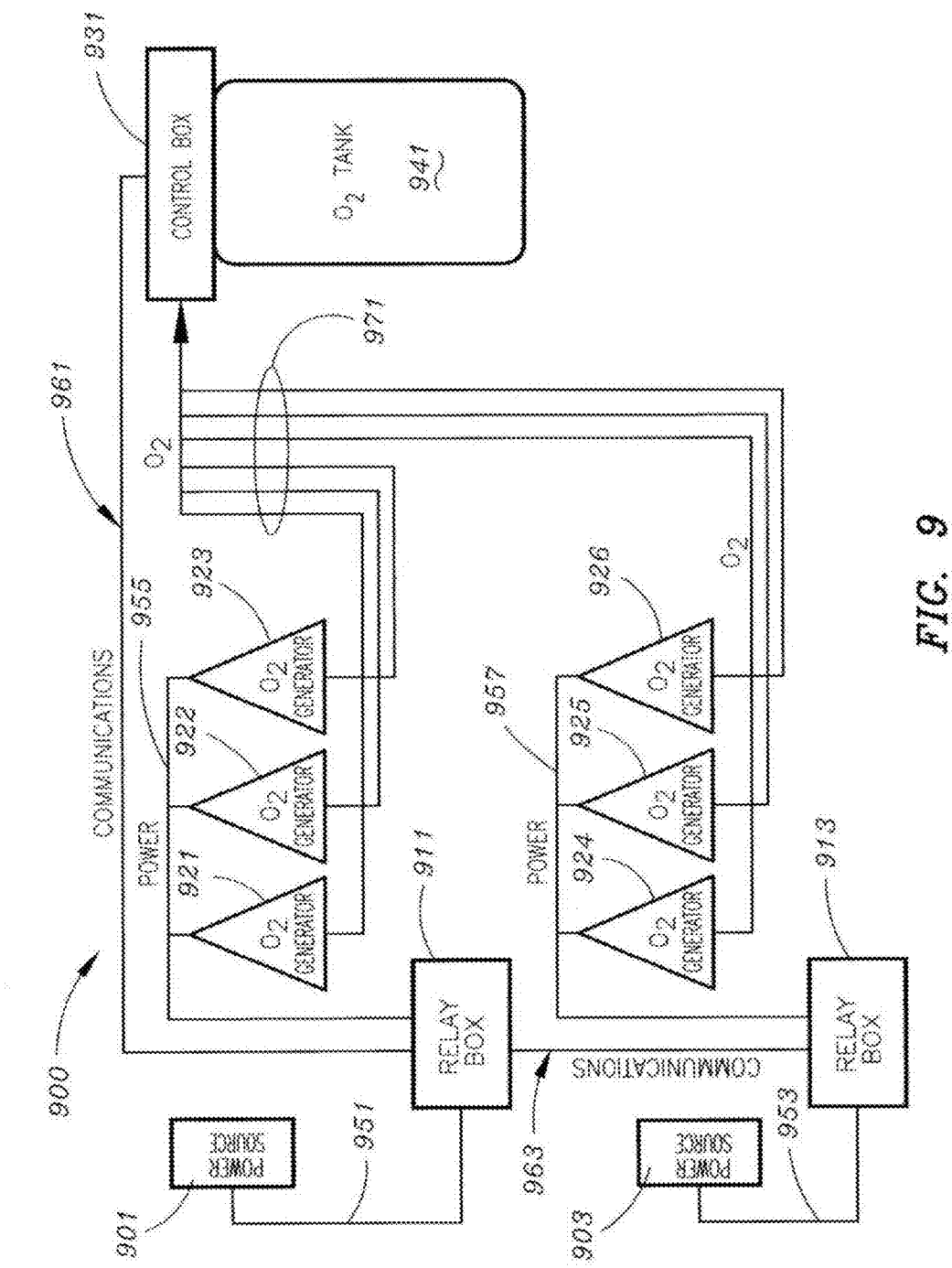
FIG. 9 shows a diagram of an embodiment of an oxygen generating system with remote relays and outlet boxes.
Figure 10:
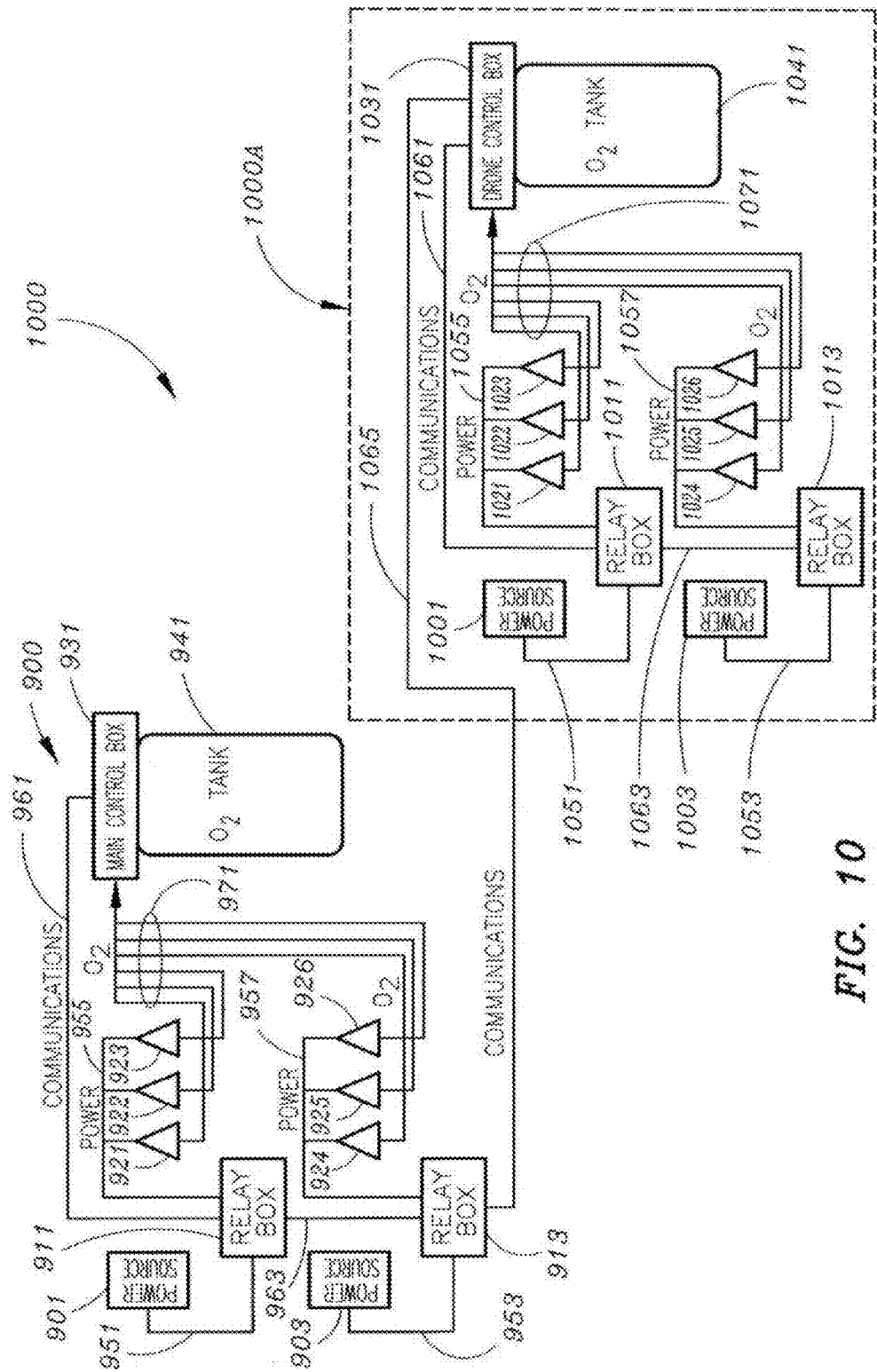
FIG. 10 shows a diagram of an embodiment of an oxygen generating system configured for modular expansion.

Referring to FIGS. 9 and 10, a diagram of an embodiment of an oxygen generating system 900 is depicted in FIG. 9. As similarly described above, the oxygen generating system may include a control box 931; an oxygen tank 941; a first relay box 911; a second relay box 913; a first power source 901; a second power source 903; oxygen generators 921-926; communication or data cables or wires 961 connecting the control box 931 to the first relay box 911; communication or data cables or wires 963 connecting the first relay box 911 to the second relay box 913; electrical lines 951 connecting the first power source 901 to the first relay box 911; electrical lines 953 connecting the second power source 903 to the second relay box 913; electrical lines 955 connecting the first relay box to a first bank of oxygen generators (e.g., 921-923); electrical lines 957 connecting the second relay box to a second bank of oxygen generators (e.g., 924-926); and oxygen piping, hoses, or tubing 971 connecting the oxygen generators 921-926 to the control box 931. The control box 931 may be communicatively coupled with the first relay box 911 and the second relay box 913 via communication cables or wires 961, 963. The control box 931 may function as a main control box (see, e.g., 1031) communicatively coupled with one or more other control boxes (see, e.g., 1031).

For example, the oxygen generating system 900 may include a 114 liter (30 gallon) oxygen storage tank (e.g., 941) and 6 oxygen generators (e.g., 921-926), each of the oxygen generators (e.g., 921-926) designed to produce approximately 10 liters of oxygen per minute (under one example of contemplated operating pressures), such that the oxygen generating system 900 may produce 60 liters of oxygen per minute while storing up to 114 liters of compressed oxygen in the oxygen storage tank (e.g., 941).

Referring to FIG. 10, the oxygen generating system 900 of FIG. 9 can be expanded indefinitely into a modular oxygen generating system 1000 as depicted in FIG. 10. The modular expandable oxygen generating system 1000 may include the oxygen generating system 900 (which may include components as previously described in reference to FIG. 9); one or more communications or data cables or wires 1065 communicatively coupling a relay box (such as the second relay box 913) of oxygen generating system 900 or the main control box 931 of the oxygen generating system 900 to a control box (such as a drone control box 1031) or a relay box (e.g., 1011, 1013) of an expansion oxygen generating system (e.g., 1000A). Some implementations may include the use of relay boxes, while other implementations may include components of the relay box (e.g., 1011, 1013) as part of the control box (e.g., 931, 1031).

The expansion oxygen generating system 1000A may include the control box (such as the drone control box 1031); an oxygen tank 1041; a first relay box 1011; a second relay box 1013; a first power source 1001; a second power source 1003; oxygen generators 1021-1026; communication or data cables or wires 1061 connecting the control box 1031 to the first relay box 1011; communication or data cables or wires 1063 connecting the first relay box 1011 to the second relay box 1013; electrical lines 1051 connecting the first power source 1001 to the first relay box 1011; electrical lines 1053 connecting the second power source 1003 to the second relay box 1013; electrical lines 1055 connecting the first relay box to a first bank of oxygen generators (e.g., 1021-1023); electrical lines 1057 connecting the second relay box to a second bank of oxygen generators (e.g., 1024-1026); and oxygen piping, hoses, or tubing 1071 connecting the oxygen generators 1021-1026 to the control box 1031. The control box 1031 may be communicatively coupled with the first relay box 1011 and the second relay box 1013 via communication cables or wires 1061, 1063 or a wireless connection. The control box 1031 may function as a drone control box or as a main control box communicatively coupled with one or more other control boxes (see, e.g., 931). In some implementations, the control box 1031 may include a controller device; in other implementations, the control box 1031 may not include a controller device. A controller device (such as a digital controller) of the main control box 931 may indirectly or directly control the first bank of oxygen generators (e.g., 1021-1023), the second bank of oxygen generators (e.g., 1024-1026), and the compressor (which may be included in the control box 1031) of the expansion oxygen generating system 1000A.

The controller device of the main oxygen generating system's control box (e.g., 931) may be configured to manage the main oxygen generating system (e.g., 900) as well as any modularly expandable expansion oxygen generating systems (e.g., 1000A). As similarly described above, the controller device of the main oxygen generating system's control box (e.g., 931) may be configured for controlling the main system oil-less air compressor and at least two main system circuits for providing power to the at least two main system groups of at least one oxygen generator, the at least two main system circuits including a first main system circuit and a second main system circuit, the first main system circuit associated with the first main system group of at least one oxygen generator and the second main system circuit associated with the second main system group of at least one oxygen generator. Additionally, the controller device of the main oxygen generating system's control box (e.g., 931) may be configured for controlling a particular expansion oxygen generating system's oil-less air compressor and at least two particular expansion system circuits for providing power to the at least two particular expansion system groups of at least one oxygen generator, the at least two particular expansion system circuits including a first particular expansion system circuit and a second particular expansion system circuit, the first particular expansion system circuit associated with the first particular expansion system group of at least one oxygen generator and the second particular expansion system circuit associated with the second particular expansion system group of at least one oxygen generator.

The modularly expandable oxygen generating system (e.g., 1000) may be configured and arranged in a multitude of manners. For example, in some implementations, the modularly expandable oxygen generating system (e.g., 1000) may be configured such that an outlet of the particular expansion system oxygen storage tank is configured to couple with the main system oxygen storage tank or with an outflow of oxygen from the main system oxygen storage tank; however, in other implementations, outlets of some or all of the storage tanks of the modularly expandable oxygen generating system (e.g., 1000) may not be coupled. The particular expansion oxygen generating system (e.g., 1000A) may be removably coupled to the main oxygen generating system. In some implementations, the expansion control box (e.g., 1031) may be a drone control box, wherein the drone control box lacks a digital controller and relies on the digital controller of the main control box (e.g., 931) of the main oxygen generating system (e.g., 900) to activate relies of the expansion oxygen generating system (e.g., 1000A). Additionally, expansion oxygen generating systems (e.g., 1000A) may include pressure sensors, wherein each pressure sensors is configured to sense pressure associated with an expansion system storage tank (e.g., 1041) and communicate the pressure via a signal to a particular controller device (such as a digital controller of the main control box 931 or the expansion control box 1031). Embodied implementations of a modularly expandable oxygen generating system (e.g., 1000) are contemplated such that particular oxygen generating subsystems (e.g., 900 or 1000A) may be concurrently and simultaneously managed while particular components of oxygen generating subsystems may operating at different pressures or have different operating requirements (such as different oxygen outflow requirements).

The modular oxygen generating system 1000 as depicted in FIG. 10 can produce oxygen much more quickly, and significantly more oxygen can be stored. For example, where each of the oxygen generating system 900 and the expansion oxygen generating system 1000A include a 114 liter (30 gallon) oxygen storage tank (e.g., 941, 1041) and 6 oxygen generators (e.g., 921-926, 1021-1026), each of the oxygen generators designed to produce approximately 10 liters of oxygen per minute (under designed operating pressures), then the modular oxygen generating system 1000 may produce 120 liters of oxygen per minute while storing up to 228 liters of compressed oxygen in the oxygen storage tank.

Subsystems of the modular generating system 1000 can be decoupled to operate as independent oxygen generating systems such oxygen generating system 900 and oxygen generating system 1000A.

Referring to FIG. 11, an embodied method 1100 associated with managing an oxygen generating system is depicted. It is contemplated that embodiments of the method 1100 may be performed by a control box or one or more controller devices of a control box. The method 1100 may include any or all of steps 1105, 1110, 1115, 1120, 1125, 1130, 1135, 1140, 1145, 1150, or 1155, and it is contemplated that the method 1100 may include additional steps as disclosed throughout, but not explicitly set forth in this paragraph. Further, it is fully contemplated that the steps of method 1100 may be performed concurrently or in a non-sequential order.

The method 1100 may include a step 1105 which comprises receiving electrical power. Step 1105 may include receiving electrical power from a single electrical circuit line (such as a nominal 220 volt line) or from two or more electrical circuit lines (such as two or more nominal 110 volt lines). The method 1100 may include a step 1110 which comprises sensing a first pressure to be less than or equal to a first startup threshold pressure, said first pressure associated with a gaseous pressure of an oil-less tank. The method 1100 may include a step 1115 which comprises providing electrical power to an oil-less air compressor. The method 1100 may include a step 1120 which comprises completing a first circuit, said first circuit for providing electrical power to a first group of at least one oxygen generator. The method 1100 may include a step 1125 which comprises sensing a second pressure to be less than or equal to a second startup threshold pressure, said second pressure associated with a gaseous pressure of the oil-less tank, wherein the second startup threshold pressure is greater than the first startup threshold pressure. The method 1100 may include a step 1130 which comprises completing a second circuit, said second circuit for providing power to a second group of at least one oxygen generator. The method 1100 may include a step 1135 which comprises sensing a third pressure to be greater than or equal to a first shutoff threshold pressure, said third pressure associated with a gaseous pressure of the oil-less tank. The method 1100 may include a step 1140 which comprises opening the first circuit. The method 1100 may include a step 1145 which comprises sensing a fourth pressure to be greater than or equal to a second shutoff threshold pressure, said fourth pressure associated with a gaseous pressure of the oil-less tank, wherein the second shutoff threshold pressure is greater than the first shutoff threshold pressure. The method 1100 may include a step 1150 which comprises opening the second circuit. The method 1100 may include a step 1155 which comprises cutting power to the oil-less air compressor.

Referring to FIG. 12, an embodied method 1200 associated with managing an oxygen generating system is depicted. It is contemplated that embodiments of the method 1200 may be performed by a control box or one or more controller devices of a control box. The method 1200 may include any or all of steps 1205, 1210, 1215, 1220, 1225, 1230, 1235, 1240, 1245, 1250, 1255, 1260, 1265, or 1270, and it is contemplated that the method 1200 may include additional steps as disclosed throughout, but not explicitly set forth in this paragraph. Further, it is fully contemplated that the steps of method 1200 may be performed concurrently or in a non-sequential order.

The method 1200 may include a step 1205 which comprises receiving a first pressure signal associated with a first pressure. The method 1200 may include a step 1210 which comprises determining the first pressure to be less than or equal to a first startup threshold pressure, said first pressure associated with a gaseous pressure of the oil-less tank. The method 1200 may include a step 1215 which comprises sending a signal to switch the oil-less air compressor on. The method 1200 may include a step 1220 which comprises sending a signal to switch a first circuit on, said first circuit for providing electrical power to a first bank of at least oxygen generator. The method 1200 may include a step 1225 which comprises receiving a second pressure signal associated with a second pressure. The method 1200 may include a step 1230 which comprises determining the second pressure to be less than or equal to a second startup threshold pressure, said second pressure associated with a gaseous pressure of the oil-less tank, wherein the second startup threshold pressure is greater than the first startup threshold pressure. The method 1200 may include a step 1235 which comprises sending a signal to switch a second circuit on, said second circuit for providing power to a second bank of at least one oxygen generator. The method 1200 may include a step 1240 which comprises receiving a third pressure signal associated with a third pressure. The method 1200 may include a step 1245 which comprises determining the third pressure to be greater than or equal to a first shutoff threshold pressure, said third pressure associated with a gaseous pressure of the oil-less tank. The method 1200 may include a step 1250 which comprises sending a signal to switch the first circuit off. The method 1200 may include a step 1255 which comprises receiving a fourth pressure signal associated with a fourth pressure. The method 1200 may include a step 1260 which comprises determining the fourth pressure to be greater than or equal to a second shutoff threshold pressure, said fourth pressure associated with a gaseous pressure of the oil-less tank, wherein the second shutoff threshold pressure is greater than the first shutoff threshold pressure. The method 1200 may include a step 1265 which comprises sending a signal to switch the second circuit off. The method 1200 may include a step 1270 which comprises sending a signal to switch the oil-less air compressor off.

It is believed that the present invention and many of its attendant advantages will be understood by the foregoing description, and it will be apparent that various changes may be made in the form, construction, and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A system for managing an oxygen generating system, wherein the oxygen generating system includes an oxygen storage tank, a compressor, and oxygen generators, the oxygen generating system configured for supplying a sustained flow of a gaseous mixture comprising mostly oxygen, the system comprising:
   a first circuit;
   a second circuit; and
   at least one controller device configured to:
   control the first circuit based at least upon at least one pressure, the first circuit for providing power to at least two oxygen generators; and
   control the second circuit for providing power to the compressor and to at least one oxygen generator.

2. The system of claim 1, wherein each of the first circuit and the second circuit is an electrical circuit on a fully dedicated circuit breaker.

3. The system of claim 1, wherein the first circuit is an electrical circuit on a fully dedicated circuit breaker.

4. The system of claim 2, wherein each fully dedicated circuit breaker is configured for up to 2400 watts of power, wherein a total amperage requirement of the first circuit is less than or equal to 20 amperes, wherein a total amperage requirement of the second circuit is less than or equal to 20 amperes.

5. The system of claim 4, wherein the at least one controller device comprises a digital controller comprising at least one processor.

6. The system of claim 4, wherein the at least one controller device comprises an analog controller.

7. The system of claim 4, wherein the at least one controller device comprises a pneumatic controller.

8. The system of claim 1, wherein the at least one controller device comprises a digital controller.

9. The system of claim 8, wherein the digital controller comprises at least one processor.

10. The system of claim 1, wherein the at least one controller device comprises an analog controller.

11. The system of claim 1, wherein the at least one controller device comprises a pneumatic controller.

12. The system of claim 1, wherein the at least one controller device comprises a first controller device and a second controller device,
    wherein the first controller device is configured to control the first circuit,
    wherein the second controller device is configured to control the second circuit.

13. The system of claim 1, further comprising a first relay and a second relay, wherein the first relay is coupled to the first circuit and the at least one controller device, wherein the second relay is coupled to the second circuit and the at least one controller device.

14. A system for managing a modularly expandable oxygen generating system, the modularly expandable oxygen generating system including a main oxygen generating system and at least one expansion oxygen generating system, the system comprising:
    at least one controller device configured to:
    manage the main oxygen generating system, wherein the main oxygen generating system includes a main system oxygen storage tank, a main system compressor, and main system oxygen generators, the main oxygen generating system configured to supply a sustained flow of a gaseous mixture comprising mostly oxygen, wherein the at least one controller device being configured to manage the main oxygen generating system includes the at least one controller device being configured to:
control a first main system circuit for providing power to at least two main system oxygen generators; and
control a second main system circuit for providing power to the main system compressor; and
manage a particular expansion oxygen generating system of the at least one expansion oxygen generating system, wherein the particular expansion oxygen generating system includes a particular expansion system compressor and expansion system oxygen generators, wherein the at least one controller device being configured to manage the particular expansion oxygen generating system of the at least one expansion oxygen generating system includes the at least one controller device being configured to:
control a first expansion system circuit for providing power to at least two expansion system oxygen generators; and
control a second expansion system circuit for providing power to the particular expansion system compressor.

15. The system of claim 14, wherein each of the first and second main system circuits is an electrical circuit on a fully dedicated circuit breaker.

16. The system of claim 14, wherein the second main system circuit is an electrical circuit on a fully dedicated circuit breaker.

17. The system of claim 15, wherein each fully dedicated circuit breaker is configured for up to 2400 watts of power, wherein a total amperage requirement of the first main system circuit is less than or equal to 20 amperes, wherein a total amperage requirement of the second main system circuit is less than or equal to 20 amperes.

18. The system of claim 17, wherein the at least one controller device comprises a digital controller comprising at least one processor.

19. The system of claim 17, wherein the at least one controller device comprises a pneumatic controller and a digital controller comprising at least one processor.

20. The system of claim 14, wherein the particular expansion oxygen generating system is communicatively coupled to the main oxygen generating system.

21. The system of claim 14, wherein the particular expansion oxygen generating system further includes a particular expansion system oxygen storage tank.

22. The system of claim 21, wherein an outlet of the particular expansion system oxygen storage tank is configured to couple with the main system oxygen storage tank or an outflow of oxygen from the main system oxygen storage tank.

23. A system for managing an oxygen generating system, wherein the oxygen generating system includes an oxygen storage tank, a compressor, and oxygen generators, the oxygen generating system configured for supplying a sustained flow of a gaseous mixture comprising mostly oxygen, the system comprising:
a first circuit;
a second circuit;
means for controlling the first circuit based at least upon at least one pressure, the first circuit for providing power to at least two oxygen generators; and
means for controlling the second circuit for providing power to the compressor and at least one oxygen generator.

\* \* \* \* \*